(12) United States Patent
Mulqueeny et al.

(10) Patent No.: US 9,636,474 B2
(45) Date of Patent: May 2, 2017

(54) ADAPTIVE CYCLING FOR RESPIRATORY TREATMENT APPARATUS

(75) Inventors: Qestra Camille Mulqueeny, Maroubra (AU); Didier Tassaux, Injoux-Genissiat (FR)

(73) Assignee: ResMed Limited, Bella Vista (AU)

( * ) Notice: Subject to any disclaimer, the term of this patent is extended or adjusted under 35 U.S.C. 154(b) by 285 days.

(21) Appl. No.: 13/819,037

(22) PCT Filed: Aug. 25, 2011

(86) PCT No.: PCT/AU2011/001093
§ 371 (c)(1),
(2), (4) Date: Feb. 26, 2013

(87) PCT Pub. No.: WO2012/024733
PCT Pub. Date: Mar. 1, 2012

(65) Prior Publication Data
US 2013/0152934 A1    Jun. 20, 2013

Related U.S. Application Data

(60) Provisional application No. 61/377,664, filed on Aug. 27, 2010.

(51) Int. Cl.
*A61M 16/00* (2006.01)
*A61M 16/06* (2006.01)
*A61M 16/08* (2006.01)

(52) U.S. Cl.
CPC ........ *A61M 16/0066* (2013.01); *A61M 16/00* (2013.01); *A61M 16/0051* (2013.01);
(Continued)

(58) Field of Classification Search
None
See application file for complete search history.

(56) References Cited

U.S. PATENT DOCUMENTS 3,916,888 A * 11/1975 Buck ..................... A61M 16/00
128/202.22
4,915,103 A * 4/1990 Visveshwara ......... A61M 16/00
128/204.21
(Continued)

FOREIGN PATENT DOCUMENTS

WO    2010/121313 A1    10/2010

OTHER PUBLICATIONS

Tassaux, D., Gainnier, M., Battisti, A., & Jolliet, P. (2005). Impact of expiratory trigger setting on delayed cycling and inspiratory muscle workload. American Journal of Respiratory and Critical Care Medicine, 172(10), 1283-1289.*

(Continued)

*Primary Examiner* — Tan-Uyen (Jackie) T Ho
*Assistant Examiner* — Joseph D Boecker
(74) *Attorney, Agent, or Firm* — Lerner, David, Littenberg, Krumholz & Mentlik, LLP

(57) ABSTRACT

A controller or processor (s) implements detection of respiratory related conditions that may serve as control logic to synchronize pressure treatment delivery with a patient's respiratory cycle. Based on data derived from sensor signals associated with the respiratory treatment, a monitoring device, detector or respiratory treatment apparatus may evaluate flow measures from a flow sensor and distinguish flow attributable to the respiratory treatment apparatus and flow attributable to patient respiratory muscles. The determination may serve as a basis of synchronization criteria that controls pressure levels from a pressure treatment apparatus, such as by evaluating the determined patient generated flow or a relationship between total flow and apparatus flow. In some embodiments, data for the cycling conditions is determined in preliminary treatment cycles during which synchronized pressure changes are controlled (Continued)

according to other cycling criteria. The new cycling conditions are then automatically initiated for control of synchronization in subsequent cycles.

28 Claims, 11 Drawing Sheets

(52) U.S. Cl.
CPC ........ *A61M 16/0069* (2014.02); *A61M 16/06* (2013.01); *A61M 16/0875* (2013.01); *A61M 2016/0027* (2013.01); *A61M 2016/0039* (2013.01); *A61M 2205/50* (2013.01); *A61M 2230/46* (2013.01); *A61M 2230/60* (2013.01)

(56) References Cited

U.S. PATENT DOCUMENTS

| | | | |
|---|---|---|---|
| 5,540,733 A * | 7/1996 | Testerman | A61B 5/1135 600/529 |
| 5,865,173 A * | 2/1999 | Froehlich | A61M 16/00 128/204.21 |
| 6,213,119 B1 * | 4/2001 | Brydon | A61M 16/00 128/204.18 |
| 6,439,229 B1 * | 8/2002 | Du | A61M 16/00 128/204.21 |
| 6,532,960 B1 | 3/2003 | Yurko | |
| 7,089,937 B2 * | 8/2006 | Berthon-Jones | A61M 16/00 128/204.18 |
| 7,128,069 B2 | 10/2006 | Farrugia et al. | |
| 2002/0023644 A1 * | 2/2002 | Berthon-Jones | A61B 5/085 128/204.22 |
| 2002/0026941 A1 * | 3/2002 | Biondi | A61M 16/00 128/204.21 |
| 2003/0168066 A1 | 9/2003 | Sallvin | |
| 2003/0192544 A1 * | 10/2003 | Berthon-Jones | A61M 16/00 128/204.18 |
| 2003/0221689 A1 | 12/2003 | Berthon-Jones | |
| 2006/0086357 A1 * | 4/2006 | Soliman | A61M 16/0051 128/204.22 |
| 2007/0089738 A1 * | 4/2007 | Soliman | A61M 16/0051 128/202.22 |
| 2007/0101992 A1 * | 5/2007 | Soliman | A61M 16/0051 128/204.21 |
| 2007/0169779 A1 * | 7/2007 | Freeman | A61M 16/12 128/204.18 |
| 2008/0000475 A1 * | 1/2008 | Hill | A61M 16/00 128/204.18 |
| 2008/0110461 A1 * | 5/2008 | Mulqueeny | A61M 16/00 128/204.23 |
| 2008/0163872 A1 * | 7/2008 | Negele | A61M 16/0051 128/204.21 |
| 2008/0202528 A1 * | 8/2008 | Carter | A61M 16/0051 128/204.23 |
| 2009/0020121 A1 * | 1/2009 | Bassin | A61M 16/00 128/204.23 |
| 2009/0229611 A1 | 9/2009 | Martin et al. | |
| 2010/0147303 A1 * | 6/2010 | Jafari | A61M 16/0051 128/204.23 |
| 2010/0236553 A1 * | 9/2010 | Jafari | A61M 16/0051 128/204.21 |
| 2011/0017214 A1 * | 1/2011 | Tehrani | A61M 16/0051 128/204.22 |
| 2011/0023878 A1 * | 2/2011 | Thiessen | A61M 16/0051 128/204.21 |
| 2011/0100365 A1 * | 5/2011 | Wedler | A61M 16/00 128/204.23 |
| 2011/0162647 A1 * | 7/2011 | Huby | A61M 16/0057 128/203.14 |
| 2012/0037159 A1 * | 2/2012 | Mulqueeny | A61B 5/085 128/204.23 |
| 2012/0226444 A1 * | 9/2012 | Milne | A61B 5/08 702/19 |
| 2012/0291785 A1 * | 11/2012 | Ramanan | A61M 16/0051 128/204.23 |
| 2015/0114396 A1 * | 4/2015 | Ramanan | A61M 16/0051 128/204.23 |

OTHER PUBLICATIONS

Yamada, Y., & Du, H. L. (2000). Analysis of the mechanisms of expiratory asynchrony in pressure support ventilation: a mathematical approach. Journal of Applied Physiology (Bethesda, Md.: 1985), 88(6), 2143-2150.*

Kondili, E., Prinianakis, G., & Georgopoulos, D. (2003). Patient-ventilator interaction. British Journal of Anaesthesia, 91(1), 106-119.*

Kondili, E., Akoumianaki, E., Alexopoulou, C., & Georgopoulos, D. (2009). Identifying and relieving asynchrony during mechanical ventilation. Expert Review of Respiratory Medicine, 3(3), 231-243. doi:10.1586/ers.09.13.*

International Search Report and Written Opinion for PCT/AU2011/001093 dated Mar. 15, 2012.

Yoshitsugu Yamada and Hong-Lin Du, Analysis of the mechanisms of expiratory asynchrony in pressure support ventilation: a mathematical approach, J Appl Physiol, 88: 2143-2150, 2000.

* cited by examiner

ADAPTIVE CYCLING FOR RESPIRATORY TREATMENT APPARATUS

CROSS REFERENCE TO RELATED APPLICATIONS

This application claims the benefit of the filing date of U.S. Provisional Patent Application No. 61/377,664 filed on Aug. 27, 2010, the disclosure of which is hereby incorporated herein by reference.

FIELD OF THE TECHNOLOGY

The present technology relates to methods and apparatus for respiratory treatment. More particularly, it relates to automated methods for controlling detection of respiratory conditions such as a patient respiratory cycle and/or for controlling changes to treatment in conjunction with a patient's respiratory cycle.

BACKGROUND OF THE TECHNOLOGY

Ensuring quality interaction between a patient and their respiratory treatment apparatus can be significant. For example, some respiratory treatment apparatus provide a higher pressure during inspiration than during expiration. In such a case, the apparatus may attempt to synchronize the generated change in pressure with the patient's respiration cycle.

For example, in the case of a pressure treatment apparatus for treatment of sleep disordered breathing (e.g., a bi-level positive airway pressure apparatus), the controller may be configured to generate a lower pressure during expiration for patient comfort. Such expiratory pressure relief is described in U.S. Pat. No. 7,128,069, the entire disclosure of which is incorporated herein by reference.

In the case of a ventilator, synchronization between a patient and the apparatus can be critical to minimize the work of breathing of the patient. Increased work of breathing caused by patient-ventilator asynchrony is associated with negative patient outcomes and has been shown to be highly prevalent; studies have shown up to 47% of ventilator delivered breaths may be asynchronous.

In some devices, detecting inspiratory flow with a flow sensor or a decrease in pressure with a pressure sensor may serve as tests for triggering the delivery of inspiratory pressure. The detection of a cessation of patient inspiration, such as by detecting a peak flow or a portion thereof, may then serve as test for cycling to an expiratory pressure level. Additionally, the running of a backup timer may serve as a basis for triggering an apparatus to deliver inspiratory pressure.

It may be desirable to develop further methods and devices for automating synchronization that may improve respiratory treatment apparatus.

SUMMARY OF THE TECHNOLOGY

Aspects of the present technology may involve methods and apparatus for a detection of a patient respiration cycle or patient respiration.

Still further aspects of the technology may involve methods and apparatus for automated determination of conditions suitable for synchronizing pressure treatment with patient respiration, such as detecting flow attributable to patient respiratory muscle effort as distinguished from either a flow attributable to a respiratory treatment apparatus or a total flow measured by a flow sensor of such an apparatus.

Additional aspects of the technology may involve methods and apparatus for synchronizing pressure treatment with patient respiration and may be based on the detection of different flow conditions.

Some embodiments of the present technology can include an automated processing method for adapting cycling of a respiratory treatment apparatus where the apparatus controls a delivery of a synchronized respiratory treatment. The method may include controlling with a processor a generation of inspiratory pressure and expiratory pressure over a first plurality of cycles. During these cycles, the setting of the expiratory pressure may be based on a first cycling criteria. The method may further involve controlling with the processor a generation of inspiratory pressure and expiratory pressure over a second plurality of cycles subsequent to the first plurality of cycles. The setting of the expiratory pressure of the second plurality of cycles may be based on a second cycling criteria that is different from the first cycling criteria and is initiated for operation subsequent to the first plurality of cycles.

Optionally, the control of the first plurality of cycles may be implemented by a learning period that is configured for determining and storing values for control of treatment in a plurality of subsequent treatment sessions. Still further, in addition to or alternatively, the control of the first plurality of cycles may be implemented in a learning period that is initiated in each treatment session.

In some embodiments, the second cycling criteria may be implemented by a function of a first inspiratory flow measure and a second inspiratory flow measure where the second inspiratory flow measure is attributable to the respiratory treatment apparatus. Optionally, the first cycling criteria may involve comparing an instantaneous flow measure to a threshold proportion of a peak flow.

In some cases, the method may further involve determining values of the second cycling criteria during the control of the first plurality of cycles. These determined values of the second cycling criteria may include an inspiratory time constant. For example, the inspiratory time constant may be a function of a determined slope of an expiratory portion of a measured flow from the first plurality of cycles. Optionally, the inspiratory time constant may be a mean of a plurality of determined slopes of expiratory portions of a measured flow from the first plurality of cycles. Still further, the inspiratory time constant may be a measured time for a proportion of a tidal volume to be delivered to the patient's respiratory system in a cycle of the first plurality of cycles. The inspiratory time constant may also be a mean of measured times for a proportion of a tidal volume to be delivered to the patient's respiratory system in the first plurality of cycles. In some cases, the determination of the inspiratory time constant may involve a multiple linear regression process to fit pressure, flow and volume data for determining a measure of resistance and compliance.

Optionally, in some embodiments of the control method, the function of the first inspiratory flow measure and the second inspiratory flow measure may include an equality of the first inspiratory flow measure and the second inspiratory flow measure. Still further, the function of the first inspiratory flow measure and the second inspiratory flow measure may include a calculated difference of the first inspiratory flow measure and the second inspiratory flow measure. In some cases, the second inspiratory flow measure may a function of a determined flow peak, a calculated respiratory resistance and a pressure treatment setting.

In some embodiments, the aforementioned control processing methodologies may be implemented by a respiratory treatment apparatus for cycling synchronized respiratory pressure treatment. The apparatus may optionally include a patient interface to direct a breathable gas and a flow generator coupled with the patient interface to generate the breathable gas in inspiratory and expiratory pressure cycles through the patient interface. The apparatus may further include a flow sensor to provide a signal indicative of flow through the patient interface. In such an embodiment, a processor may be coupled with the flow generator and the flow sensor.

Additional embodiments of the present technology may also involve an automated processing method for cycling a respiratory treatment apparatus that controls a delivery of a synchronized respiratory treatment. In the method, a first flow measure with a flow sensor may be determined. The method may also involve determining a second flow measure attributable to the respiratory treatment apparatus. The method may also involve evaluating, with a processor, a cycling criteria as a function of the first flow measure and the second flow measure.

In some such embodiments, the evaluation of the cycling criteria may be a further function of a tolerance coefficient. Optionally, the determining of the second flow measure that is attributable to the respiratory treatment apparatus may involve an operation to calculate the second flow measure as function of an inspiratory resistance value and an inspiratory time constant value. In some cases, the method may also include calculating the inspiratory resistance value. This calculating of the inspiratory resistance value may be done as a function of airway pressure and flow. This airway pressure may be a difference of a positive end expiratory pressure and an airway pressure following a peak in a measure of respiratory flow. Still further, the calculating of the second flow measure may be a further function of a ventilator time constant and/or a further function of a pressure support setting.

In some cases, the evaluation of the cycling criteria may include assessing an equality of the first flow measure and the second flow measure. The evaluation of the cycling criteria may also involve calculating a difference of the first flow measure and the second flow measure. Furthermore, the evaluation of the cycling criteria may further involve comparing the difference to a threshold. The threshold may optionally be zero.

In some embodiments of the technology, the methods may also include controlling setting of an expiratory pressure based on the evaluation of the cycling criteria. This expiratory pressure may be a positive end expiratory pressure.

Moreover, the method may also involve controlling generation of inspiratory pressure and expiratory pressure over a first number of cycles where the setting of the expiratory pressure is based on a first cycling criteria. During the first number of cycles, an inspiratory time constant may be determined as a function of flow measures. A second cycling criteria may then be set as a function of the determined inspiratory time constant. This second cycling criteria may then be implemented to control generation of expiratory pressure over a second number of cycles subsequent to the first number of cycles.

In some cases, the determined inspiratory time constant may comprise a slope of an expiratory part of a curve represented by the flow measures. This may even be a mean slope.

Optionally, the first cycling criteria may include a threshold proportion of flow and the second cycling criteria may include the cycling criteria of the function of the first flow measure and the second flow measure attributable to the respiratory treatment apparatus.

As with other embodiments, the control method may be implemented in a respiratory treatment apparatus for cycling synchronized respiratory pressure treatment. Such an apparatus may include a patient interface to direct a breathable gas and a flow generator coupled with the patient interface to generate the breathable gas in inspiratory and expiratory pressure cycles through the patient interface. A flow sensor of the apparatus may provide a signal indicative of patient flow through the patient interface. In addition, a processor, coupled with the flow generator and the flow sensor, may be configured to control some or all of the methodologies previously described.

Still further embodiments of the technology, may involve an automated processing method to determine a signal indicative of patient respiration. Such a method may include determining a first inspiratory flow measure with a flow sensor. The method may also include determining a second inspiratory flow measure attributable to the respiratory treatment apparatus. The method may also include determining, with a processor, a patient flow measure as a function of the first inspiratory flow measure and the second inspiratory flow measure. This patient flow measure may then represent flow attributable to patient respiratory muscles.

In some cases, the determination of the second inspiratory flow measure attributable to the respiratory treatment apparatus may involve calculating the second inspiratory flow measure as function of an inspiratory resistance value and an inspiratory time constant value. It may also involve calculating the inspiratory resistance value. For example, the inspiratory resistance value may be calculated as a function of airway pressure and flow. In such a case, the airway pressure may comprise a difference of a positive end expiratory pressure and an airway pressure associated with a peak in a measure of respiratory flow. Still further, the calculating of the second inspiratory flow measure may be a further function of a ventilator time constant. Moreover, the calculating of the second inspiratory flow measure may be a further function of a pressure support setting. In some cases, the determining of the patient flow signal may include calculating a difference of the first inspiratory flow measure and the second inspiratory flow measure.

In some embodiments, these methodologies may be implemented by a monitoring apparatus that determines a signal indicative of patient respiration. Such an apparatus may include a controller having at least one processor to access data representing a measured flow of breathable gas from a flow sensor, the controller may then be configured, such as with a processor, to implement some or all of the aforementioned methodologies.

Some embodiments of the present technology involve an automated processing method to determine a signal indicative of patient respiration for synchronization of a respiratory treatment apparatus. The method may include determining a first inspiratory flow measure with a flow sensor. The method may also include determining a second inspiratory flow measure. The method may also include determining, with a processor, a patient respiration measure as a function of the first inspiratory flow measure, the second inspiratory flow measure and an estimate of resistance and compliance derived from an expiratory portion of a flow measure of the flow sensor. The patient respiratory measure may represent patient respiratory muscle effort. The method may also include determining of a timing for switching a pressure treatment based on the respiration measure.

Some embodiments of the method may further include calculating a resistance value for the estimate. The calculating of the resistance value may involve a function of airway pressure and flow. Further embodiments may also include calculating a compliance value for the estimate. The calculating of the resistance and compliance values may involve a multiple linear regression processing of an expiratory breath data portion where the expiratory breath data portion begins with expiration and ends before a next inspiration. The ending before the next inspiration may be a percentage of the tidal volume expired.

In some cases, these methods may be implemented as a monitoring apparatus to determine a signal indicative of patient respiration for synchronization of a respiratory treatment. The apparatus may include a controller having at least one processor to access data representing a measured flow of breathable gas from a flow sensor. The controller being further configured to perform the steps of these methods.

Some embodiments of the present technology may involve an automated processing method for cycling a respiratory treatment apparatus that controls a delivery of a synchronized respiratory treatment. Such a method may optionally include determining a flow measure with a flow sensor. The method may also include determining a pressure measure with a pressure sensor. The method may then further include determining, with a processor, an estimate of muscle effort as a function of the flow measure and pressure measure. Moreover, the method may include deriving, with the processor, a cycling control signal as a function of the estimate of muscle effort. In some cases, the determining of the estimate is a further function of an estimate of respiratory resistance and compliance. Optionally, a peak value of the control signal may be determined. In such a case, the method may also involve cycling the respiratory treatment apparatus as a function of a proportion of the peak value and the control signal. In some such embodiments, deriving of the control signal may involve setting the control signal to equal the estimate of muscle effort if the estimate of muscle effort is increasing. Optionally, the deriving of the control signal may involve setting the control signal to zero upon detection of inspiration or if the estimate of muscle effort is decreasing.

In some such embodiments, the estimate of respiratory resistance and compliance may be determined as a function of a portion of patient expiration. Optionally, the estimate may be derived from pressure, flow and volume measures taken during the portion of patient expiration. In some such cases, the derived estimate may be produced by multiple linear regression processing of the pressure, flow and volume measures taken during the portion of patient expiration beginning at patient expiration and ending when approximately ninety percent of a tidal volume has been expired.

These methodologies may optionally be implemented by a respiratory treatment apparatus for cycling synchronized respiratory pressure treatment. Such an apparatus may then include a patient interface to direct a breathable gas, a flow generator coupled with the patient interface to generate the breathable gas in inspiratory and expiratory pressure cycles through the patient interface, a flow sensor to provide a signal indicative of patient flow through the patient interface, a pressure sensor to provide a signal indicative of pressure at the patient interface and a processor, coupled with the flow generator, the pressure sensor and the flow sensor. The processor may then be configured to control the methodologies.

In another form, the technology may involve a respiratory treatment apparatus for switching synchronized respiratory pressure treatment. The apparatus may include a patient interface to direct a breathable gas, a flow generator coupled with the patient interface to generate the breathable gas in inspiratory and expiratory pressure cycles through the patient interface, an electro-optical sensor for non-invasively measuring diaphragmatic muscle activity and a processor, coupled with the flow generator and the sensor. The processor may then be configured to control a determination of muscle effort signal with the sensor and a derivation of a switching control signal, such as a triggering signal or cycling signal, as a function of the muscle effort signal.

In some such cases, the processor may further control a determination of a peak value of the control signal. Optionally, the processor may further control cycling the respiratory treatment apparatus as a function of a proportion of the peak value and the control signal. In some such cases, the derivation of the control signal may involve setting the control signal to equal the muscle effort signal if the muscle effort signal is increasing. Still further, the derivation of the control signal may also include setting the control signal to zero upon detection of inspiration or if the muscle effort signal is decreasing. Optionally, the controller may be further configured to cycle a pressure treatment controlled by the apparatus as a function of the switching control signal. Optionally, the controller may be further configured to trigger a pressure treatment controlled by the apparatus as a function of the switching control signal.

Further embodiments and features of the technology will be apparent from the following detailed disclosure, claims and drawings.

BRIEF DESCRIPTION OF THE DRAWINGS

The present technology is illustrated by way of example, and not by way of limitation, in the figures of the accompanying drawings, in which like reference numerals refer to similar elements including.

DETAILED DESCRIPTION

The present technology involves methods for detection of a patient's respiratory cycle or effort associated therewith and/or the synchronization of respiratory treatment apparatus with the respiratory cycle. In some embodiments, automated methods may be implemented for inspiratory activity monitoring (e.g., inspiratory effort). These methods may be implemented in processing apparatus, such as a respiratory treatment apparatus (e.g., ventilator or bi-level positive airway pressure apparatus.) For example, the methods may be applied during or for pressure support ventilation, such as by a ventilator having a pressure support (PS) mode. In such an example, the methods may be implemented to render the apparatus or ventilator capable of synchronizing the patient's and the ventilator's inspiratory to expiratory cycling, in a cycle-by-cycle, real time, non-invasive manner. The methodologies may be based on mathematical modeling of the inspiratory flow generated by both the patient and the ventilator and determined with a flow sensor. Thus, the processing methods may be implemented to distinguish (a) the flow generated by patient respiratory muscles from (b) the flow generated by the treatment apparatus that are both contained within a flow signal generated by a flow sensor of an apparatus during pressure treatment. The methodologies of the apparatus may employ real-time acquisition and processing of various data reflecting respiratory mechanics and ventilator performance characteristics. The methodologies may also be employed to adapt cycling criteria during or for respiratory treatment.

Figure 1:
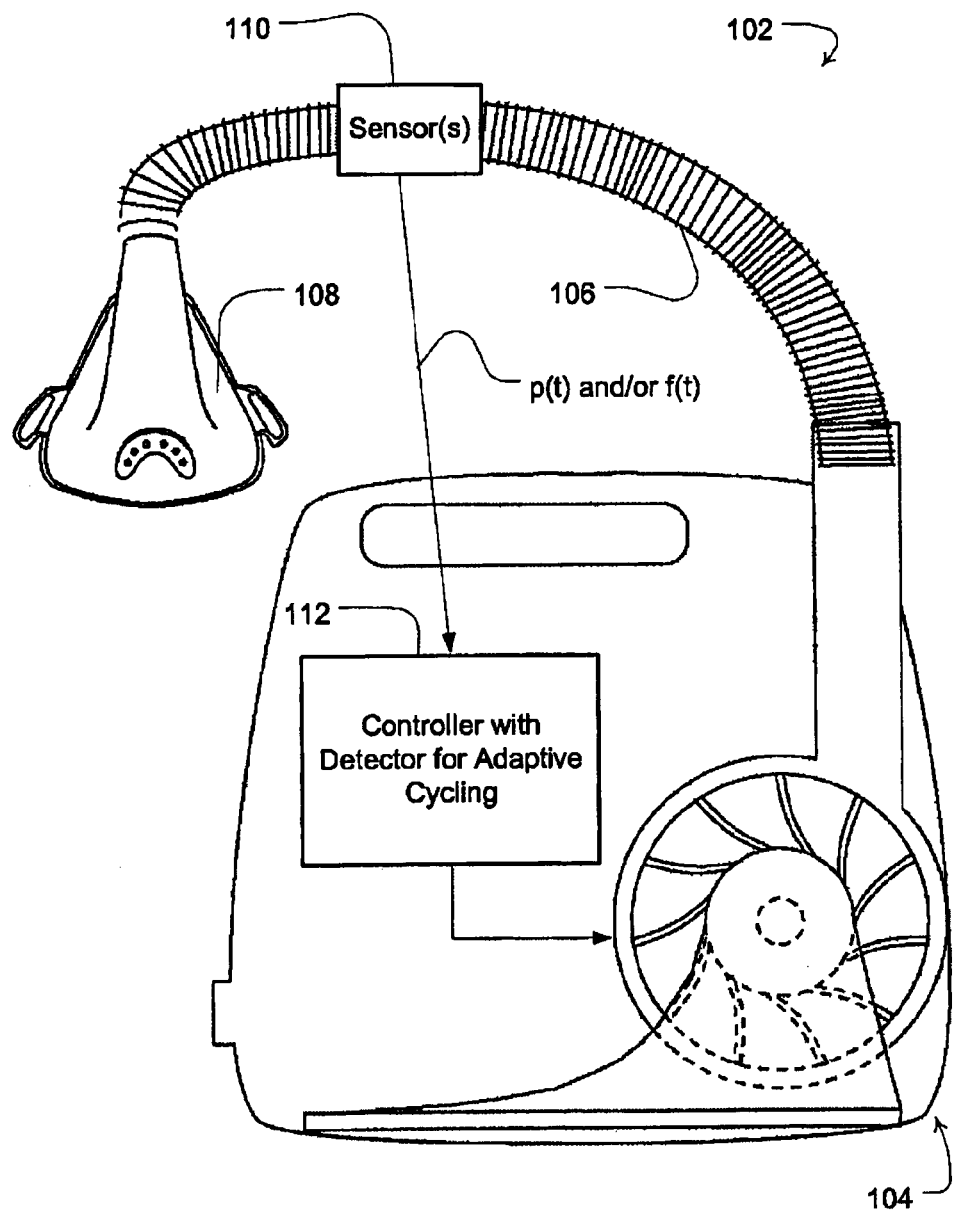
FIG. 1 is an block diagram of an example respiratory treatment apparatus with adaptive cycling of the present technology.

An example respiratory treatment apparatus 102 with adaptive cycling technology is illustrated in FIG. 1. Typically, the apparatus may have a controller implemented with a cycle detector 112, such as a programmed processor. The detector, may access data or signals from one or more sensors 110 associated with a respiratory treatment apparatus that provide control signals suitable for synchronizing a respiratory treatment. The treatment may be provided from a flow generator 104 such as a servo-controller blower, and may provide a pressurized gas delivered to a mask 108 via a tube 106 of a patient interface. For example, the data may be based on sensors 110 such as flow f(t) and/or pressure p(t) signals taken from a flow sensor and/or pressure sensor of such an apparatus. The sensors 110 may be located in the mask 108, in the tube 106 or the flow generator 104 or combinations of these locations. Based on this data the detector 102 may then distinguish patient flow from apparatus flow, determine and evaluate cycling criteria based thereon and control delivery of pressure based on the cycling conditions.

Figure 2:
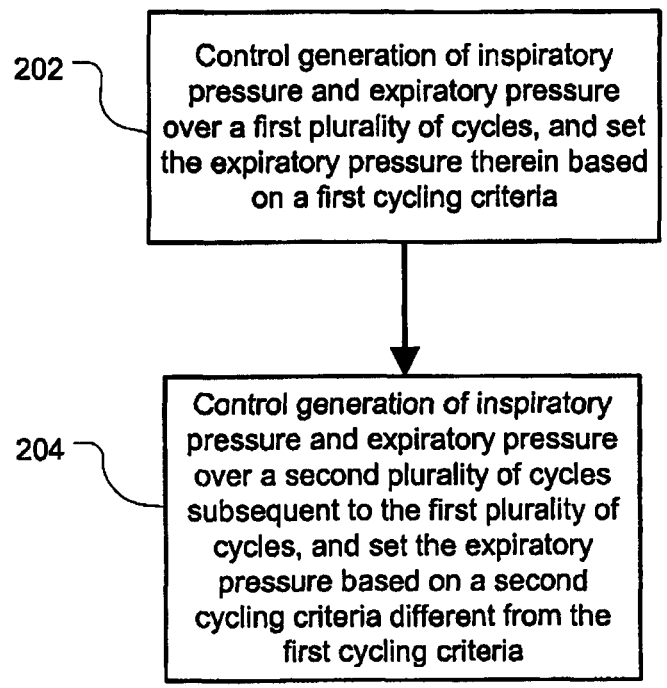
FIG. 2 is an flow chart with an example methodology that may be implemented in some embodiments of the cycling technology of the apparatus of FIG. 1.

For example, in some embodiments an apparatus with the detector 112 may implement a methodology illustrated in the flow chart of FIG. 2. In the method at 202, the apparatus may control a generation of inspiratory pressure and expiratory pressure over a first plurality of cycles. In this controlled generation of pressure, the apparatus may set the expiratory pressure based on a first cycling criteria. For example, the cycling criteria may be a comparison of an instantaneous patient flow measure to a flow threshold (e.g., a fraction of a peak patient flow.) Optionally, the cycling criteria may involve a comparison of an instantaneous pressure measure to a pressure threshold or it may involve a comparison of a tidal volume to a volume threshold. At 204, the apparatus may thereafter control a generation of inspiratory pressure and expiratory pressure over a second plurality of cycles subsequent to the first plurality of cycles. In the subsequent cycles, the apparatus may set the expiratory pressure based on a second cycling criteria. This subsequent cycling criteria may be different from the first cycling criteria. For example, this subsequent cycling criteria may be based on determined respiratory mechanics as discussed in more detail herein, which may be based on data measured during the first plurality of cycles. Thus, the subsequent cycling criteria may be enabled for operation in later cycles, subsequent to processing of the first plurality of cycles, and not be enabled for the prior or initial cycles. In this sense, the subsequent cycling criteria may be initiated for operation in latter cycles. In such embodiments, as discussed in more detail herein, the cycling criteria can be adapted during treatment and may be re-evaluated in the event of a detection of certain changes in the system, such as automated pressure setting changes.

Figure 3:
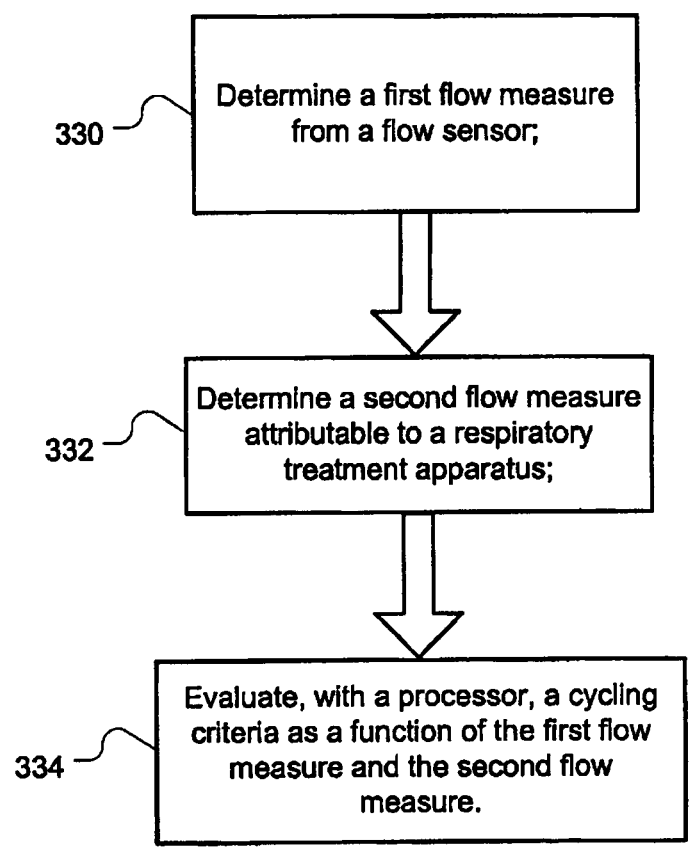
FIG. 3 is another flow chart with an example methodology that may be implemented in some embodiments of the cycling technology of the apparatus of FIG. 1.

In some embodiments of the technology, such a cycling criteria may be adapted in accordance with a methodology illustrated by the flow chart of FIG. 3. For example, at 330, a processor may determine a first flow measure from a flow sensor. Such a measure may be based on a filtered signal from the flow sensor and may represent a total flow in a patient interface or mask of a respiratory treatment apparatus. At 332, a processor may determine a second flow measure that is attributable to the respiratory treatment apparatus. For example, such a measure may be based on data from a signal of a flow sensor and/or pressure sensor. In some embodiments as discussed in more detail herein, computation of such a flow measure attributable to flow of the respiratory treatment apparatus may be based on a determined inspiratory resistance that may optionally be calculated from measures of pressure and flow associated with a peak of inspiration. Then, at 334, a processor may evaluate a cycling criteria as a function of the first flow measure and the second flow measure. For example, as discussed in more detail herein, such an evaluation may involve a determined difference between the measures or an evaluation of an equality between them.

Modeling of Flow and the Respiratory System

Some such embodiments of the present cycling technology may be based on mathematical modeling of the respiratory system. In this regard, the respiratory system may be likened to a linear mono-compartmental system of resistance R and compliance C (e.g., C=1/E where E=elastance of the system). At all times, the pressure at the system's inlet (where P=airway pressure) can be expressed as the following equation of motion of the respiratory system:

$$P = E \cdot V + R \cdot \dot{V} \qquad \text{equation (1)}$$

Where:
P is the pressure;
E is the elastance (e.g., 1/C where C is compliance);
R is resistance;
is volume expressed as the integral of flow; and
$\dot{V}$ is the patient flow.

In such as case, inertial forces due to acceleration (e.g., inertance) can be overlooked when respiratory rate is less than 2 Hz. Indeed, pressure due to inertia for a respiratory rate between 0-120 L/min is less than 0.001 cmH$_2$O.

Hence, at each time point (t), equation (1) can be written as follows:

$$P(t) = E \cdot V(t) + R \cdot \dot{V}(t) \qquad \text{equation (1A)}$$

In the case of the use of a respiratory treatment apparatus configured to provide pressure, such as a ventilator providing pressure support (PS), pressure P(t) is generated both by the ventilator (Pps) and by the patient's respiratory muscles (Pmus):

$$Pps(t)+Pmus(t)=E \cdot V(t)+R \cdot \dot{V}(t) \quad \text{equation (2)}$$

Where:
Pps(t) is the pressure attributable to the ventilator's pressure support;
Pmus(t) is the pressure attributable to the patient's respiratory muscles;
Pressure generated by the ventilator (e.g., Pps) may have an increasing exponential function over time which can be expressed as:

$$Pps(t) = Pps_{max}\left(1 - e^{-\frac{t}{\tau v}}\right) \quad \text{equation (3)}$$

where:
t is time;
$\tau V$ is a ventilator time constant; and
$Pps_{max}$ may be a set inspiratory pressure level or a pressure maximum.
Respiratory muscular pressure (Pmus) is a second order polynomial function that can be written as:

$$Pmus(t) = Pmus_{max} - Pmus_{max}\left(1 - \frac{t}{ti}\right)^2 \quad \text{equation (4)}$$

Where:
$Pmus_{max}$ is a maximal muscular pressure during a given inspiratory effort;
t is time; and
ti is a duration of an inspiratory effort.
Thus, equation (2) may then become:

$$\left(1 - e^{-\frac{t}{\tau v}}\right)Pps + Pmus_{max} - Pmus_{max}\left(1 - \frac{t}{ti}\right)^2 = \quad \text{equation (5)}$$
$$E \cdot V(t) + R \cdot \dot{V}(t)$$

The equation describing volume changes over time V(t) is not described here as it would be understood by a person skilled in the art. However, its first derivative is, by definition, the equation of the inspiratory flow, so that the inspiratory flow equation can be written as:

$$\dot{V}(t) = \underbrace{\frac{\left(e^{-\frac{t}{\tau p}} - e^{-\frac{t}{\tau v}}\right) \cdot Pps_{max}}{R \cdot \left(1 - \frac{\tau v}{\tau p}\right)}}_{A} + \quad \text{equation (6)}$$
$$\underbrace{\frac{(2\ Pmus_{max})}{R} \cdot \left(\frac{\tau p}{ti}\right) \cdot \left[\left(1 + \frac{\tau p}{ti}\right) \cdot \left(1 - e^{-\frac{t}{\tau p}}\right) - \frac{t}{ti}\right]}_{B}$$

where:
$\tau p$ is a patient inspiratory time constant (e.g., $\tau p$, =R/E with R being inspiratory resistance and E being elastance of the respiratory system);
$\tau V$ is a ventilator time constant;
$Pps_{max}$ is a set pressure support level or maximum pressure (e.g., a pressure level attributable to an IPAP or a difference between an IPAP level and EPAP level such as in the case of a device that may provide a bi-level pressure treatment for sleep disordered breathing patients or respiratory insufficiency patients);
$Pmus_{max}$ is a maximal muscular pressure (for a given inspiratory effort);
R is an inspiratory resistance; and
Ti is a duration of the inspiratory effort.
As shown above, part A of equation (6) corresponds to the equation of ventilator or apparatus-generated flow:

$$\dot{V}Pps(t) = \frac{\left(e^{-\frac{t}{\tau p}} - e^{-\frac{t}{\tau v}}\right) \cdot Pps_{max}}{R \cdot \left(1 - \frac{\tau v}{\tau p}\right)} \quad \text{equation (7)}$$

while Part B of equation (6) corresponds to patient-generated flow:

$$\dot{V}mus(t) = \frac{(2\ Pmus_{max})}{R} \cdot \left(\frac{\tau p}{ti}\right) \cdot \left[\left(1 + \frac{\tau p}{ti}\right) \cdot \left(1 - e^{-\frac{t}{\tau p}}\right) - \frac{t}{ti}\right] \quad \text{equation (8)}$$

Accordingly, from these equations, it may be understood that flow measured in the airways at a given time point may equal or approximate the sum of both ventilator or apparatus generated flow (e.g., equation (7)) and patient generated flow (e.g., equation (8)). Thus, some embodiments of the present technology may be based on such a relationship. For example, a determination of patient flow may be based from a determination of total measured flow (e.g., from a flow sensor) and flow attributable to a respiratory treatment apparatus. In some cases, this can involve calculating a difference between the total flow and the flow attributable to the respiratory treatment apparatus. However, as discussed in more detail herein, other evaluations may be implemented based on the aforementioned relationship without necessarily calculating the difference.

Example Applications of Flow Relationship

Thus, in some embodiments, the function shown in equation (6) above, may be implemented with automated processing apparatus to trace the flow-time curve. In such a function, some or all of the following variables may serve as input to the equation:
a patient inspiratory time constant ($\tau p$);
an apparatus or ventilator time constant ($\tau v$);
an apparatus generated pressure ($Pps_{amx}$) such as the set pressure support PS;
a muscle generated pressure ($Pmus_{max}$);
an inspiratory effort duration (ti); and
a resistance (R).
The processing of the function, or discrete aspects of it, may then be evaluated to determine flow attributable to a patient and/or flow attributable to the apparatus that is or was providing pressure to the patient.

Accordingly, there may be some practical considerations and observations associated with such an analysis. For example, the determination of an apparatus or ventilator generated flow (as shown in example equation (7)) applies certain factors dependant upon the type of apparatus. In this regard, apparatus flow ($\dot{V}Pps(t)$) can depend on input or prior determination of an inspiratory pressure level, which, in the case of a ventilator providing pressure support (PS)

may be a set inspiratory pressure support (PS) level. Similarly, it may further depend on input or prior determination of a time constant attributable to the flow delivered by the apparatus (e.g., a ventilator time constant) and an inspiratory time constant of the patient's respiratory system (τp).

In regard to the apparatus time constant of this function, such as the ventilator time constant, it may be taken to be an increasing exponential function of the ventilator pressure curve, such that it is independent of the patient's inspiratory effort and respiratory system mechanics. Theoretically, it depends solely on the pneumatic and mechanical features of the apparatus or ventilator and especially on inspiratory valve function (kinetics of valve opening, ramps slope pressure, shape of the rising pressure curve). In the example model herein, the shape of the inspiratory pressure curve has been approximated as an increasing exponential function. Further knowledge of the inspiratory valve's regulatory algorithms (as designed by the manufacturer of a given apparatus) permits modifications to the current model. Moreover, the methodologies may benefit from a consistent control (and knowledge) of the ventilator or apparatus features, especially regarding an inspiratory valve or related inspiratory control, so that the shape of the pressurization curve is not only known, but can remain stable over the actual range of patient inspiratory efforts. Nevertheless, the apparatus time constant (e.g., τv) can be estimated by a non-linear regression (increasing exponential) of the inspiratory pressure curve obtained on bench studies and be pre-determined for each particular apparatus.

In some cases, the shape of the pressure curve can change when an inspiratory valve or an apparatus provides a limited flow. Such a situation can be encountered in case of considerable inspiratory effort by the patient. Such an event may not be accounted for in the example function.

With regard to the inspiratory resistance (R) and the patient inspiratory time constant (τp), these can markedly influence the shape of the inspiratory flow curve. In the case of a Pressure Support Ventilator (PSV), their assessment can be difficult with non-invasive techniques.

The determination of respiratory muscle generated flow (as shown in example equation (8)) applies certain factors dependant upon the patient. In this regard, the muscle attributable flow ($\dot{V}Pmus(t)$) can depend on maximal pressure generated by the respiratory muscles, the inspiratory effort duration and the mechanical features of the respiratory system.

In this regard, the maximal pressure generated by the respiratory muscles ($Pmus_{max}$) may refer to that pressure maximum that is actually provided throughout inspiration, rather than the maximal inspiratory pressure ($PI_{max}$) that these muscles can potentially generate. With respect to measurement of inspiratory effort, in clinical practice, measurement of inspiratory effort characteristics (duration and intensity) can be difficult to determine by non-invasive techniques. Nevertheless, these characteristics are an important element to monitor in patients undergoing mechanical ventilation.

In the present example model, the curve shape of muscular pressure is a second order polynomial function. This choice may be justified by recordings performed in healthy subjects. It is however presently known that the actual shape is more of an increasing exponential function, and even more so as the inspiratory airway resistance is elevated.

As with the components of the ventilator-generated inspiratory flow, the flow driven by respiratory muscles depends strongly on the mechanical characteristics of the respiratory system.

Example Monitoring Embodiments

Accordingly, the aforementioned techniques may be implemented for non-invasive monitoring of inspiratory effort such as with a monitoring device that detects inspiratory effort from data generated by a flow sensor. For example, it may be implemented by a special purpose computer that accesses data previously determined by a device having a flow sensor or a respiratory treatment apparatus such as a ventilator having a flow sensor.

For example, it may be implemented with a ventilator that is configured to control pressure to provide Pressure Support Ventilation (PSV). During pressure treatment (such as PS), total inspiratory flow measured in the airways (e.g., $\dot{V}(t)$) may be considered equal to the sum of inspiratory flow due to ventilator pressurization (part A of equation (6)) and inspiratory flow due to inspiratory pressure generated by the respiratory muscles (part B of equation (6)). The time-course of inspiratory flow can be written as follows:

$$\dot{V}(t) = \dot{V}Pps(t) + \dot{V}Pmus(t) \qquad \text{equation (9)}$$

where:
$\dot{V}Pps(t)$ is an example form of apparatus flow and may be determined or understood to be the following:

$$\dot{V}Pps(t) = \frac{\left(e^{-\frac{t}{\tau p}} - e^{-\frac{t}{\tau v}}\right) \cdot Pps_{max}}{R \cdot \left(1 - \frac{\tau v}{\tau p}\right)}$$

and
$\dot{V}Pmus(t)$ is an example form of patient muscle generated flow and may be determined or understood to be the following:

$$\dot{V}mus(t) = \frac{(2Pmus_{max})}{R} \cdot \left(\frac{\tau p}{ti}\right) \cdot \left[\left(1 + \frac{\tau p}{ti}\right) \cdot \left(1 - e^{-\frac{t}{\tau p}}\right) - \frac{t}{ti}\right]$$

As previously mentioned, in these equations the variables may optionally be as follows:
τp=the inspiratory time constant of the patient respiratory system (τp=R/E or R*C, where R=inspiratory resistance, E=respiratory system elastance and C=compliance);
τV=ventilator time constant;
$Pps_{max}$=set pressure support level;
$Pmus_{max}$=maximal muscular pressure (for the analyzed inspiratory effort);
R=inspiratory resistance; and
ti=inspiratory effort duration;

In clinical practice and with some approximations, a determination or a graphic representation of apparatus flow $\dot{V}Pps(t)$ is possible, whereas some non-invasive methods may not be able to determine muscle flow $\dot{V}Pmus(t)$. However, with a value of $\dot{V}(t)$ that is known (e.g., by actual measurement of total flow during inspiration by a flow sensor of the apparatus or ventilator), $\dot{V}Pmus(t)$ can then be determined such as by a simple subtraction method as follows:

$$\dot{V}Pmus(t) = \dot{V}(t) - \dot{V}Pps(t) \qquad \text{equation (10)}$$

In this manner, the time-course of inspiratory flow generated by the respiratory muscles can be obtained for display or further analysis. Moreover, features of inspiratory effort can be determined from data that represents this time-course of inspiratory flow attributable to patient inspiration. For example, duration and intensity: (e.g., semi-quantitatively) and its evolution over the time may be automatically processed or evaluated. Moreover, these may be processed in a monitoring device on a cycle-by-cycle basis, since all determinants of equation $\dot{V}Pps(t)$ can be determined or calculated once inspiratory flow reaches a maximal inspiratory flow ($\dot{V}(t)_{peak}$) as described in more detail herein.

In this particular approach, the subtraction provides an output that may be considered an approximation of the flow generated by the respiratory muscles. Thus, it might also include some quantity attributable to any error resulting from the simplifications inherent to the model on which it is based. However, in some embodiments, it may be possible to provide another discrimination of inspiratory effort based on a model that accounts for corrections in the non-linearity of airways resistance, ventilator time constant and online measurement of respiratory mechanics. Generally, a determination of the mechanical characteristics of the respiratory system is the main conceptual difficulty of this previously described model since inspiratory resistance and an inspiratory time constant are evaluated by approximations. This might tend to suggest that such a method may not be suitable for implementation. Nevertheless, surprisingly the method yields satisfying results, such as when it is implemented for automated treatment control. For example, it does so when it is applied to automatic setting of an expiratory trigger (i.e., automatic cycling setting) in the example embodiments discussed in more detail herein.

Figure 4:
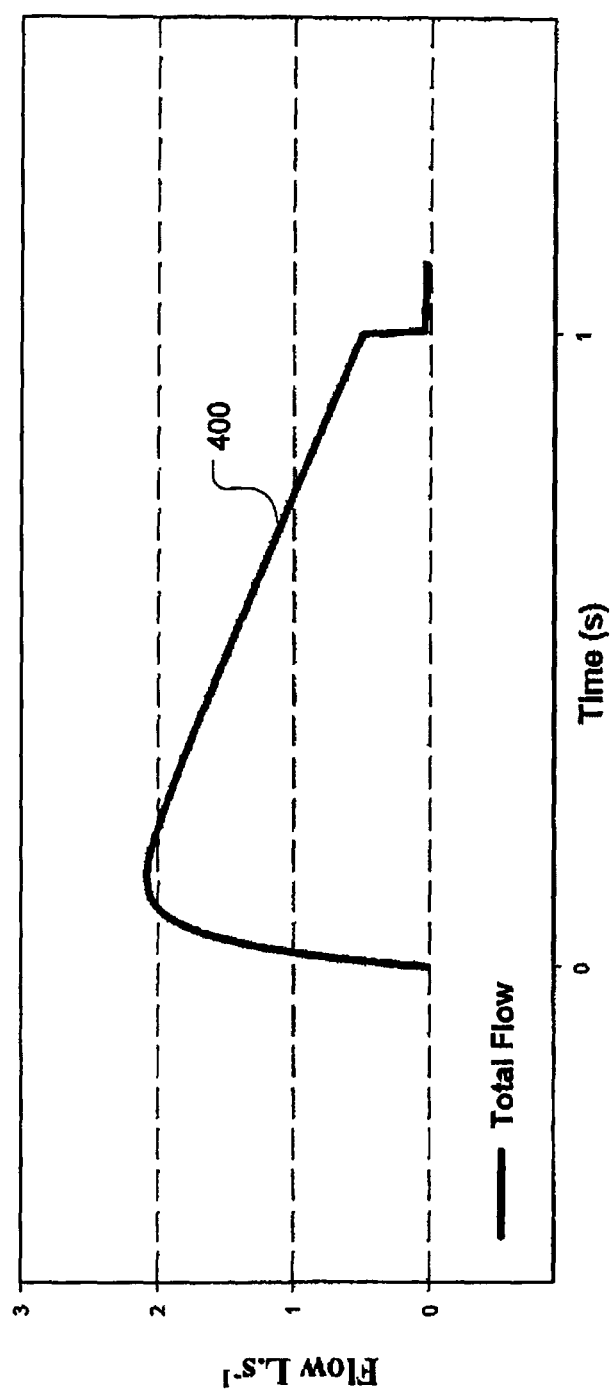
FIG. 4 is a graph of a total flow signal that may be determined by an apparatus during treatment.
Figure 5:
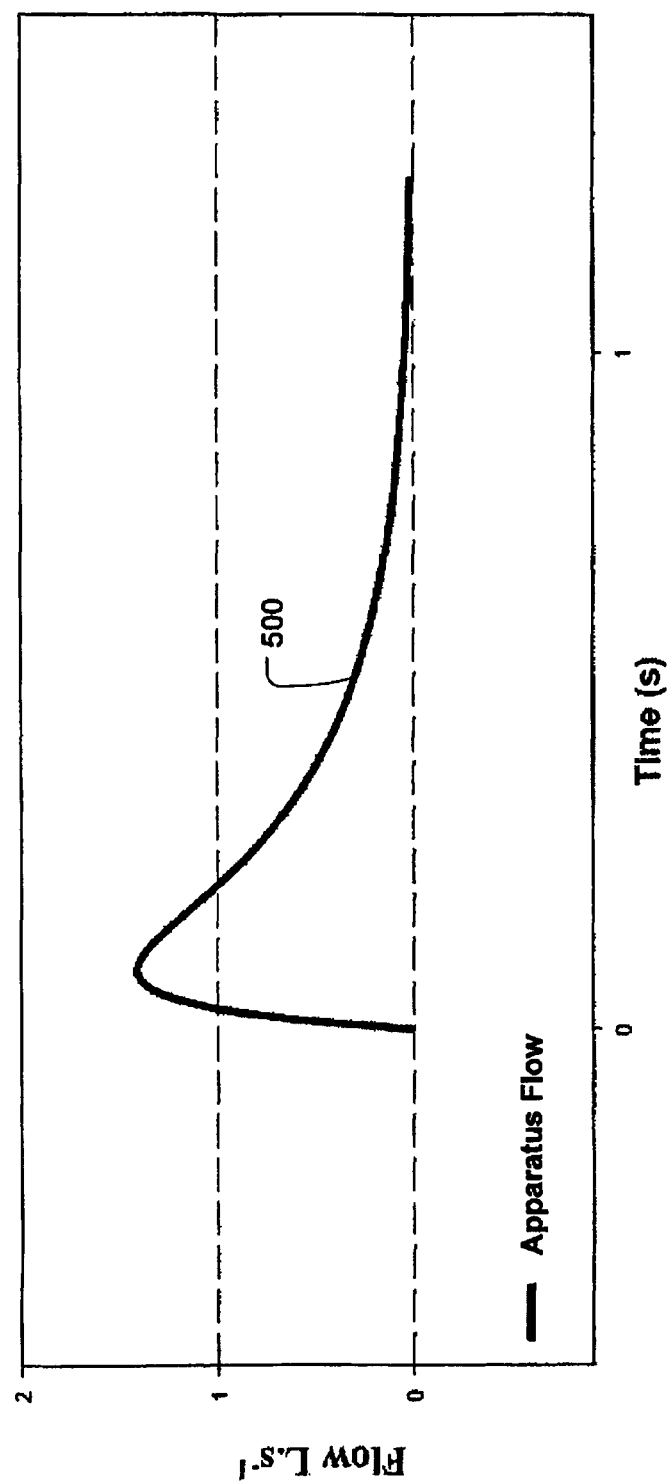
FIG. 5 is a graph of a flow signal attributable to a treatment apparatus that may be determined by an apparatus during treatment.
Figure 6:
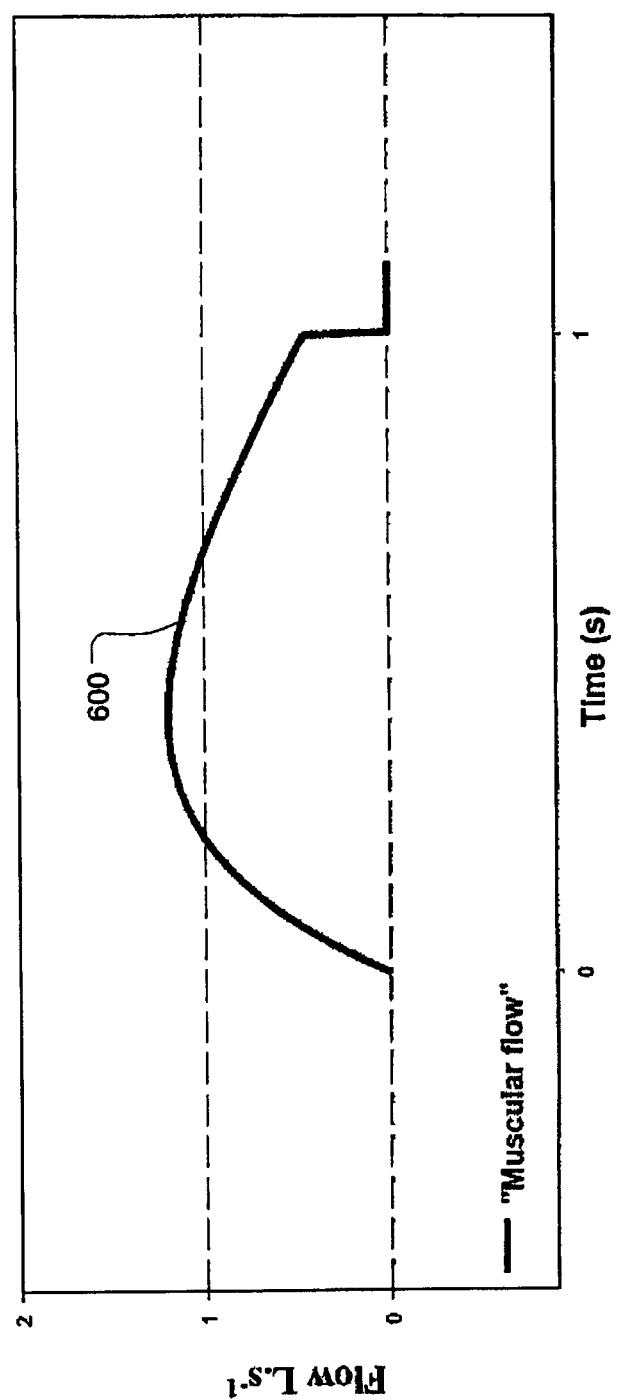
FIG. 6 is a graph of a flow signal attributable to patient respiratory muscle effort that may be determined by an apparatus during treatment.
Figure 7:
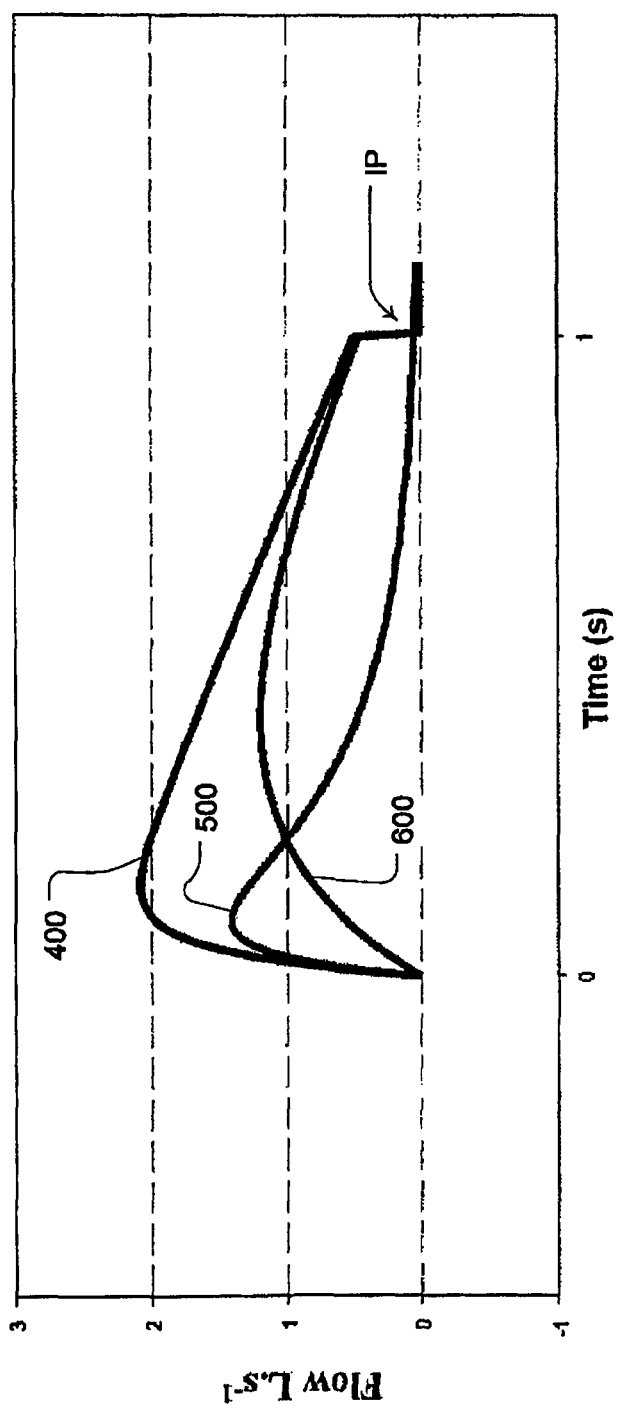
FIG. 7 is a graph of the signals from FIGS. 4-6 plotted on a common time scale.

Furthermore, in association with the monitoring features of the apparatus and for other purposes such as clinician or patient review, these flow determinations for the respiratory treatment apparatus and/or the patient's respiratory muscles, as well as the values involved in the calculations and determinations, may be recorded and reported by the monitoring device. Thus, the information may be recorded as data in the memory of a device and/or output to a display apparatus. Similarly, it may be transmitted (e.g., via wired or wireless communication) for review or analysis with other processing apparatus. For example, the flow attributable to the apparatus, the flow attributable to the patient and/or the total flow may be displayed on a graph. For example, a graphic representation of one or more of $\dot{V}Pmus(t)$, $\dot{V}Pps(t)$, $\dot{V}(t)$, such as the example graphs illustrated in FIGS. 4-9 may be generated by the monitoring apparatus or respiratory treatment apparatus for display to a user of the device or clinician. To this end, a total flow signal 400 such as a measure flow from a flow sensor (e.g., $\dot{V}(t)$) is shown in the graph of FIG. 4 during the course of a breathing cycle. A calculated signal attributable to a respiratory treatment apparatus or apparatus flow signal 500 such as a ventilator flow signal (e.g., $\dot{V}Pps(t)$) is shown in the graph of FIG. 5 during the course of a breathing cycle. A calculated signal attributable to a patient muscular flow or muscular flow signal 600 (e.g., $\dot{V}Pmus(t)$)) is shown in the graph of FIG. 6 during the course of a breathing cycle. Each of these three signals is also plotted on a common time scale in the graph of FIG. 7 to show the relationship between them.

Example Embodiments for Automated Cycling

As previously discussed, in some applications of the technology, automated processing may control flow cycling, such as with an expiratory flow trigger, during pressure treatment in a respiratory treatment apparatus. Such cycling may, for example, be implemented in a ventilator, such as one that provides Pressure Support Ventilation (PSV). Thus, it may synchronize the end of the apparatus' inspiratory cycle with the end of the patient's inspiratory effort. The processing may be based on the flow subtraction methodology or modifications thereof such as those described herein.

In this regard, pressure support may be provided in a pressure-controlled ventilatory mode by an apparatus during which the apparatus performs the following sequence:

1) detection of inspiratory effort (e.g., by measured detection of initiation of inspiratory flow and/or by a detection of a decrease in airway pressure);

2) airway pressurization, (e.g., in accordance with an increasing exponential function), the time constant of which can be programmed or determined by non-linear regression (depending on the ventilator's design);

3) pressurization stops (e.g., when an instantaneous measured value of the flow reaches a preset value such as a flow criteria of cycling or flow expiratory trigger) with a return to the preset positive end expiratory pressure level.

In such embodiments, the flow expiratory trigger may be considered a level (e.g., programmed into the apparatus software) of inspiratory flow at which the ventilator interrupts inspiratory pressurization. Chronologically, the level may be reached after maximal inspiratory flow ($\dot{V}(t)_{peak}$), on the decreasing part of the flow curve. Commonly, this value can be a fraction of the peak of inspiratory flow ($\dot{V}(t)_{peak}$), which may be a set or fixed value, or the result of computations, depending on the ventilator's design.

Figure 8:
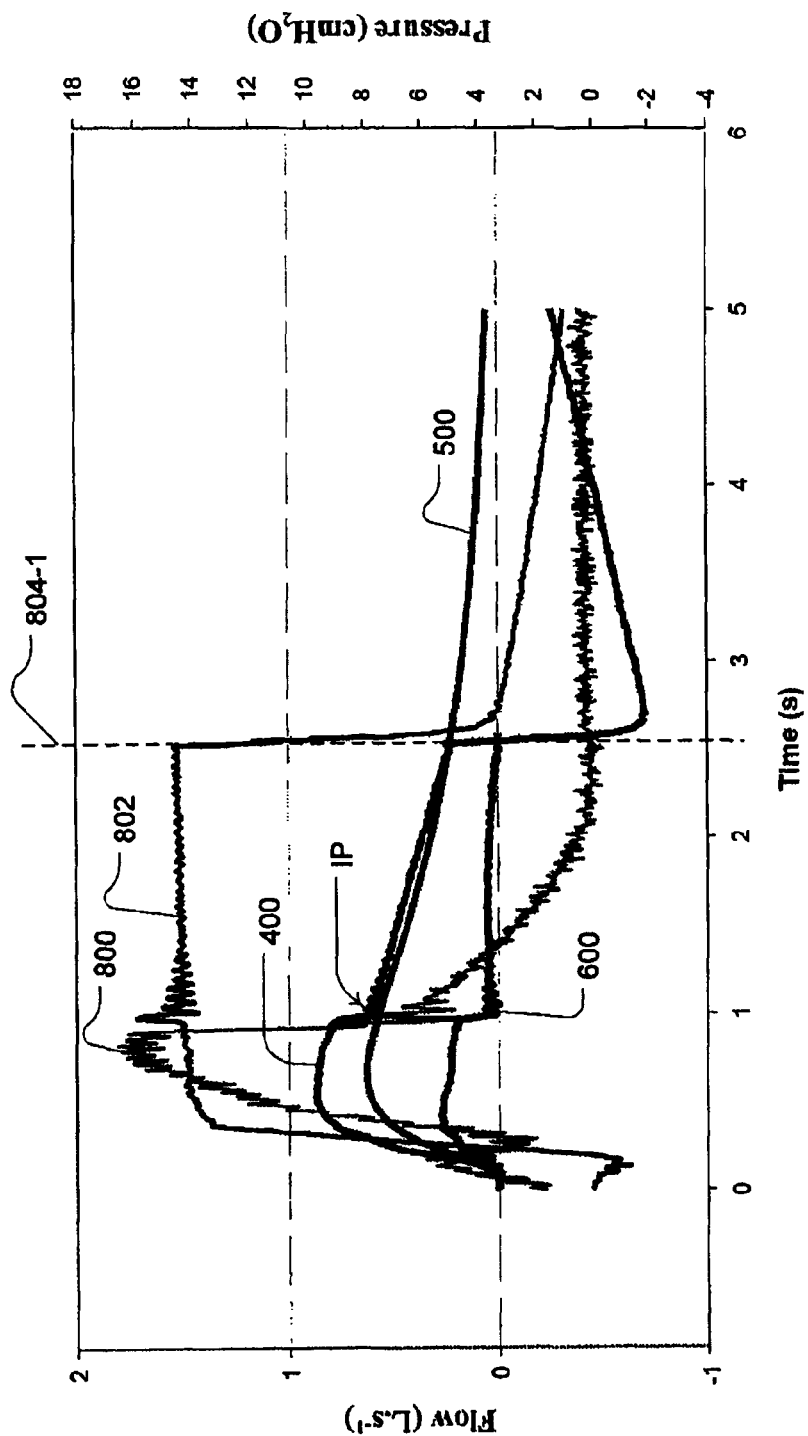
FIG. 8 is a graph of pressure and flow signals determined in some embodiments of the present cycling technology.

Such a cycling of treatment pressure based on peak flow at a cycling time 804-1 is illustrated in FIG. 8. In the graph, the total flow signal 400, apparatus flow signal 500, muscular flow signal 600 are graphed along with a delivered pressure signal 802 which may be a pressure measured at the patient's airway. Also graphed is a respiratory muscle effort signal 800 determined from diaphramatic Electromyography (EMG). In the displayed cycle, the pressure change at the time of cycling (e.g., cycling time 804-1) is executed when the total flow signal falls to a threshold that is 0.25 of the peak value of inspiratory flow for the cycle. As evident from the figure, this expiratory change of pressure may occur out of true synchronization with the patient's cycle. In this sense, it occurs after the time of a reduction in the measured respiratory muscle effort signal 800 that may be taken as an indication of the end of inspiration.

As previously described, inspiratory flow at the end of patient inspiratory effort depends on (a) pressure apparatus features (pressure level (e.g., PS setting) and pressure curve shape or rise time), (b) respiratory mechanics (inspiratory resistance, inspiratory time constant) and (c) various characteristics of the patient's inspiratory effort (duration, intensity and muscular pressure time slope). The end of inspiratory effort can be estimated by application of the flow subtraction method such that during inspiration:

$$\dot{V}Pmus(t) = \dot{V}(t) - \dot{V}Pps(t)$$

Where:

$\dot{V}Pmus(t)$ is the inspiratory flow generated by the respiratory muscles;

$\dot{V}(t)$ is the total measured inspiratory flow;

$\dot{V}Pps(t)$ is the inspiratory flow generated by the ventilator.

In some embodiments, the total flow, $\dot{V}(t)$, can be directly measured by the apparatus or ventilator's flow sensor and the apparatus flow, $\dot{V}Pps(t)$, can be calculated after determination of the patient's inspiratory resistance and inspiratory time constant, such as for the particular breath, and which may be based on the pressure data and flow data.

When V̇Pmus(t)=0, patient contribution to inspiratory flow can be considered to be nil and thus, the patient inspiratory effort of a particular respiratory cycle may be considered to be terminated. Thus, a cycling criterion based on the assessment of V̇Pmus(t)=0, or the assessment of V̇(t)−V̇Pps(t)=0 or even the assessment of V̇(t)=V̇Pps(t) may be implemented to control the apparatus. Graphically, this corresponds to the moment when the V̇(t) curve intersects with the V̇Pps(t) curve. This may be seen at intersection point IP in FIG. 7 or FIG. 8.

An automated evaluation for such a cycling criteria may involve the following processing:

(1) The total flow V̇(t) may be measured. Such a V̇(t) measurement, as well as its graphic representation, may be implemented by an intensive care or home ventilator as well as other respiratory treatment apparatus.

(2) Determine flow attributable to the apparatus such as by computation of V̇Pps(t). In some embodiments, this may be achieved with the following calculation:

$$\dot{V}Pps(t) = \frac{\left(e^{-\frac{t}{\tau p}} - e^{-\frac{t}{\tau v}}\right) \cdot Pps_{max}}{R \cdot \left(1 - \frac{\tau v}{\tau p}\right)}$$

This calculation may further involve a determination of the following values:

(a) τp determination:

In some embodiments, the inspiratory time constant, τp, may be considered the time required for a percentage (e.g., a percent in a range of 60 and 65 such as about 63%) of the tidal volume to enter the respiratory system. Indeed, with a constant pressure, the curve of volume entering the respiratory system over time during inspiration is an increasing exponential function. Thus, the time constant may be assessed by, for example, measuring the time with a timer from the start of inspiration until the time that a tidal volume for the current breath reaches the percentage threshold. In some embodiments, this feature may be determined by calculation of the slope of an expiratory part of the flow-volume curve associated with the particular breathing cycle.

In still further embodiments, the inspiratory time constant may be determined as a function respiratory mechanics such as a function of respiratory resistance (R) and respiratory compliance (C) (e.g., $\tau_p = R(cmH_2O \cdot L^{-1} \cdot s) \times C(L/cmH_2O)$). Optionally, such a determination may be substantially made from flow data from a flow sensor and pressure data from a pressure sensor. For example, an automated methodology for the determination of resistance and/or compliance by multiple linear regression may be that or adapted from the methodologies described in International Patent Application No. PCT/AU2010/000457, filed 22 Apr. 2010, the entire disclosure of which is incorporated herein by reference. A description of an example methodology is contained in more detail in a separate section herein.

(b) τv Determination

In some embodiments, the treatment apparatus time constant (τv) may be obtained by non-linear regression (increasing exponential) of the pressure curve. Typically, such a time constant τv should be determined for each different ramp slope setting of the pressure delivery apparatus and utilized in association with the setting. For example, such values may be pre-determined and accessed from a memory store of the apparatus. Thus, they can be automatically selected when the user sets pressure delivery characteristics of the apparatus. In some cases, if the ramp pressure of an apparatus is programmed with an increasing exponential function, τv values are known. If the pressure curve shape is based on a substantially different function, the equation for the apparatus flow (V̇Pps(t)) may be appropriately modified to account such different curves. However, even without such modifications, the quantitative consequences of using the exponential-function approximation are typically quite small.

(c) R Determination

Inspiratory resistance may be obtained by any suitable method. For example, it may be determined by the methods described herein in relation to International Patent Application No. PCT/AU2010/000457. However, in some embodiments, it may be determined by processing of the following ratio:

$$R = \frac{\Delta P}{\dot{V}(t)_{peak}}$$

Where:

ΔP=Paw−PEEP;

Paw=measure airway pressure at or following the time of a determined inspiratory flow peak (V̇(t)$_{peak}$) of the breathing;

PEEP=positive end expiratory pressure, which may be a setting of the apparatus.

This resistance determination as a result of its peak related time position will provide a value that may be considered a maximal inspiratory resistance.

Optionally, the calculation of the inspiratory flow due to apparatus pressurization V̇Pps(t) may be plotted, and optionally displayed as a graph, on a flow time curve.

Figure 9:
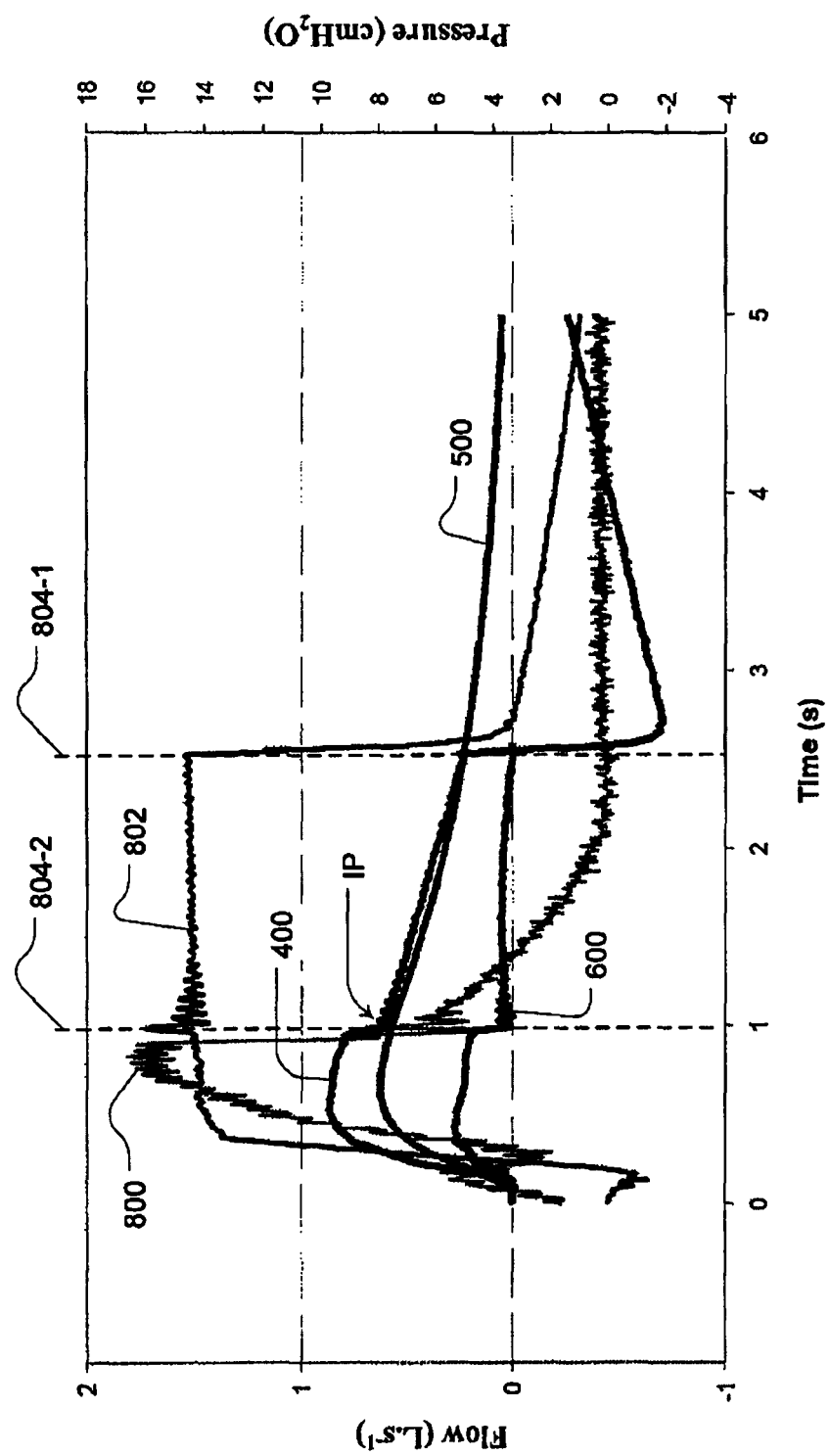
FIG. 9 is the graph of FIG. 8 showing further cycling criteria for some embodiments of the current technology.

3. Determine the flow attributable to the patient inspiratory muscle effort, such as by computation of V̇Pmus(t). In this regard, some embodiments of the present technology may determine V̇Pmus(t) in a calculation that subtracts the V̇Pps(t) curve from the V̇(t) curve. In this regard, when V̇(t)−V̇Pps(t)=0, muscular activity contribution to the total inspiratory flow is zero and thus, inspiratory effort can be considered as terminated. In other words, if this cycling condition is reached, that is, the difference meets a zero threshold, the apparatus may cycle into the expiratory phase. Optionally, the zero threshold may be modified (i.e., raised or lowered) to implement a tolerance coefficient as discussed in more detail herein. A graph of the pressurization termination in accordance with the aforementioned criteria may approximately correspond to the intersection IP of V̇(t) and V̇Pps(t) as shown in FIG. 9. FIG. 9 is a graph that contains the same signals from the graph of FIG. 8. However, an additional cycling time 804-2 associated with the cycling criteria of the subtraction based model described herein is also illustrated. As is evident from the difference in time of cycling time 804-1 and cycling time 804-2, the flow subtraction based model described herein may serve as a control to trigger expiratory pressure in greater synchrony with actual patient expiration since time 804-2 more closely corresponds with actual measured respiratory muscle effort signal 800. In such a case, the drop in pressure at time 804-1 would occur instead at or about time 804-2. Moreover, this automated cycling may be made without data of an EMG, and may instead rely on calculations that are based on pressure and flow data from non-invasive flow and pressure sensors such as those described herein.

In some embodiments, this cycling criteria for termination of pressurization, and which may optionally initiate pressure control to meet a PEEP pressure level, may involve evaluation of an equality, such as between total measured flow and apparatus generated flow, and may be further based on an optional tolerance coefficient. For example, the cycling criteria or expiratory trigger may involve an evaluation of the following equality:

$$\dot{V}(t) = \dot{V}Pps(t) \pm Ct$$

Where:

Ct is a tolerance coefficient.

Such a coefficient may be determined by empirical analysis. It may be in a suitable range to allow for compensation of inaccuracies in measurements and computations stemming from the model or apparatus. Thus, the coefficient may optionally be implemented as an adjustable input value to be set with the input controls of an apparatus in which the cycling criteria is programmed. When the equality is true, with or without the optional coefficient, it can serve as a condition for pressure cycling.

With the aforementioned techniques, a fixed flow threshold for cycling may be computed, e.g., with a processing apparatus, such as by determining $\dot{V}Pps(t)$, and by manually setting a flow cycling threshold of a treatment apparatus with the computed value for use during a treatment setting. Thus, the processing apparatus that computes the cycling criteria need not be integrated in a treatment apparatus such as a pressure support type ventilator. However, the computations and measurements implemented for this sequence can be achieved in real time. Moreover, a cycle-by-cycle setting may be implemented with the methodologies. Thus, they may be implemented for automatic setting as described in more detail herein. Indeed, with the automated methodologies), cycling can be adjusted during respiratory treatment not only based on patient effort characteristics but also based on changes in respiratory mechanics. Moreover, this dynamic respiratory mechanics based setting of synchronization criteria may be processed in a non-invasive manner (e.g., with external flow and/or pressure sensors).

Additional Embodiments for Automated Cycling

As previously mentioned, the methodologies previously described may be implemented in a respiratory treatment apparatus to permit the apparatus to automatically set, and optionally continuously re-set, its cycling criteria, such as during a particular treatment session with the apparatus. A further example of such an apparatus may be implemented with a processing sequence that follows. This example is based on a pressure support ventilator. However, it will be recognized that other respiratory treatment apparatus that deliver changes in pressure in synchrony with a patient respiratory cycle may also be implemented with adaptations of such a processing methodology.

1. Initially, the treatment apparatus may be set to a particular pressure (e.g., a pressure support (PS) level setting). A particular ramp slope may also be set. These settings may be associated with a $\tau v$ value in the data store or memory of the apparatus. Thus, these initial settings may also automatically designate a $\tau v$ value for determination of the cycling criteria.

2. The apparatus may then deliver a number of pressure cycles, (e.g., a number of cycles (n) in a range of 1 and 30, such as five PS cycles). These cycles may be designated herein as $C_1$, $C_2$, $C_3/C_4$, $C_5$ ... $C_n$. During cycling of this initial delivery of pressure, a default cycling criteria may control the synchronized changes in pressure. For example, the apparatus may be programmed to implement a cycling criteria based on a comparison of an instantaneous flow value and a fixed portion of a peak flow (e.g., 0.25 $\dot{V}(t)$peak). Other known cycling criteria may also be implemented in these preliminary cycles. However, the cycling criteria during these preliminary cycles will typically be different from the respiratory mechanics based cycling criteria such as that previously described in conjunction with equation (10). Rather, values for the subsequent cycling criteria will be developed (e.g., measured or calculated) within the preliminary cycles and then afterwards, be enabled for control of the operation of subsequent apparatus cycles. Optionally, the preliminary cycles may be implemented as a discrete learning period, such as when the patient is awake, which may be activated by a clinician. During the learning period, the cycling related values are learned and stored so that they may be used when one or more treatment sessions are subsequently initiated for the patient. Thus, they may be recorded for later use. For example, these values may be learned in a different learning apparatus and the data for cycling may then be transferred to a particular treatment apparatus for use by the patient in subsequent treatment sessions or the values may be learned in a particular treatment apparatus during an initial clinical session and then be used in that particular treatment apparatus in subsequent treatment sessions. However, the preliminary cycles may also optionally be automatically or manually initiated in a period of use of a treatment apparatus that is part of, or precedes, a treatment session or may be manually or automatically re-initiated during such a treatment session with the apparatus.

3. Thus, in the preliminary cycles, an initial $\tau p$ determination is made such as from data representing a Flow-Volume curve. For example, such a methodology may be implemented according to the following process:

3.1 measure flow at flow sensor for determination of flow volume data (e.g., V(t);

3.2. trace flow-volume data (e.g., detect breath cycle including inspiration and expiration portions of each cycle);

3.3. Determine patient inspiratory time constant $\tau p$. This may be detected by determining the slope of expiratory part of flow-volume curve or by other calculations previously discussed;

3.4. Repeat sequence for each of the preliminary breathing cycles (e.g., C1 to Cn);

3.5. Optionally, a mean $\tau p$ ($\tau p_m$) may be determined from each $\tau p$ from preliminary cycles ($\tau p_{c1}$ ... $\tau p_{cn}$);

4. The processor of the device will then initiate operation of an "AUTO-SYNC" sequence for the cycles subsequent to the preliminary cycles (e.g., $C_{n+1}$ or C6 where n=5). During this operation a cycling criteria such as one based on equation (10) will become operable for controlling cycling of the device. For example, the processing for subsequent cycles may involve the following operations:

4.1. Detect inspiratory trigger (e.g., $t_{ini}$=temporal position of inspiratory effort detection.) This will coincide with controlled initiation of pressurization by the controller of the apparatus);

4.2. Detect peak flow from the flow signal (e.g., identification of $\dot{V}V(t)$peak which may be calculated as the point of transition to the decreasing phase of the $\dot{V}(t)$ signal);

4.3. Determination of pressure for resistance computation, if resistance is utilized; (e.g., determine $\Delta P$). This process may involve measuring airway pressure at the time of the peak flow such as by analysis of data taken with a pressure sensor. An end expiration pressure value, which may be based on a device setting value, may then be subtracted from the measured airway pressure at the peak. (e.g., Paw−PEEP at $\dot{V}(t)peak$);

4.4. Determine resistance for the current breathing cycle (e.g., $R_{(c6)}$. For example, this may be calculated according to the following equation or by other suitable methods $$\left(e.g., R = \frac{\Delta P}{\dot{V}(t)peak}\right);$$

4.5. Determine flow attributable to the apparatus. For example, this may be accomplished by computation of $\dot{V}Pps(t)$ as in equation 7 above where: $R=R_{(C6)}$, $\tau v$ is the value selected in operation 1 above, ti=1; Pps=pressure level or PS level selected in operation 1 above, $Pmus_{max}=0$, $\tau p=mean(\tau p_{(C1-C5)})$;

4.6. Assess flow attributable to patient; (e.g., computation of $\dot{V}V(t)-\dot{V}Pps(t)$ from tini).

4.7. Evaluate cycling criteria (e.g., if $\dot{V}(t)-\dot{V}Pps=0$, then control the pressure so as to transition to deliver the expiratory pressure (e.g., set a "CYCLE OFF" flag));

5. The prior "AUTO-SYNC" operation of 4 above may be repeated for further cycles. However, optionally, the operation of 4 may be performed for one cycle and the processing of cycles thereafter (e.g., $C_{n+1+i}$ for i greater than equal to 1) may involve the following operations:

5.1. Detect inspiratory trigger (e.g., $t_{ini}$=temporal position of inspiratory effort detection.) This will coincide with controlled initiation of pressurization by the controller of the apparatus).

5.2. Detect peak flow from the flow signal (e.g., identification of $\dot{V}(t)peak$ which may be calculated as the point of transition to the decreasing phase of the $\dot{V}(t)$ signal);

5.3. Determination of pressure for resistance computation, if resistance is utilized; (e.g., determine $\Delta P$). This process may involve measuring airway pressure at the time of the peak flow such as by analysis of data taken with a pressure sensor. An end expiration pressure value, which may be based on a device setting value, may then be subtracted from the measured airway pressure at the peak. (e.g., Paw−PEEP at $\dot{V}V(t)peak$);

5.4. Determine resistance for the current breathing cycle (e.g., $R_{cn+1+i}$). For example, this may be calculated according to the following equation or by other suitable methods $$\left(e.g., R = \frac{\Delta P}{\dot{V}(t)peak}\right);$$

5.5. Determine flow attributable to the apparatus. For example, this may be accomplished by computation of $\dot{V}Pps(t)$ as in equation 7 above where: $R=R_{Cn+1+i}$, $\tau v$ is the value selected in operation 1 above, ti=1; Pps=pressure level or PS level selected in operation 1 above, $Pmus_{max}=0$, and $\tau p$ is taken from the calculation associated with the prior cycle rather than a mean (e.g., $\tau p_{(cn+i)}$);

5.6. Assess flow attributable to patient (e.g., computation of $\dot{V}(t)-\dot{V}Pps(t)$ from $t_{ini}$);

5.7. Evaluate cycling criteria (e.g., if $\dot{V}(t)-\dot{V}Pps=0$ ($\pm Ct$), then control the pressure so as to transition to deliver the expiratory pressure (e.g., set a "CYCLE OFF" flag);

6. If there is a modification of the treatment pressure level such as the pressure quantity controlled by the PS level setting or of the rise time (e.g., PS slope), then the $\tau V$ may be automatically reset for subsequent cycle calculations (e.g., operations of 4.5 or 5.5 above).

Respiratory Mechanics Determination

In some of the aforementioned embodiments, an automated determination of resistance R and/or compliance C values may be implemented according to the methodologies described in International Patent Application No. PCT/AU2010/000457. This determination may be made by a multiple linear regression method. Multiple linear regression (MLR) extends simple linear regression and is used to describe the relationship between a single response variable with a set of two or more explanatory variables. The relationship is linear and can be written in its basic form as $$Y_i = \beta_0 + \beta_1 x_{i,1} + \beta_2 x_{i,2} + \ldots + \beta_k x_{i,k} \epsilon_i$$

where the random errors $\epsilon_i$, i=1, 2, ..., n, are normally distributed random variables with zero mean and constant variance $\sigma^2$.

The patient-ventilator system can be modeled as a single compartment such that the total driving pressure is the sum of the elastic and resistive properties of the system. This can be described by a first order differential equation as follows:

$$P_{tot} = R\dot{V}(t) + \frac{V(t)}{C} + P_0$$

where $P_{tot}$ is the driving pressure, $\dot{V}$ is the flow through the airways, V is the volume displaced, R is the airway resistance, C is the compliance of the respiratory system, and $P_0$ is the pressure at end-expiration which is the sum of the applied external PEEP and internal PEEP of the patient. By defining the driving pressure as the single response variable and flow and volume as the explanatory variables, a processor can apply MLR to measured data to determine the parameters R and C.

The noise in the system is predominantly random produced by turbulent flow and the ventilator turbine. The latter also produces deterministic and cyclostationary components that may influence the outcome of the model. However within the frequency range of interest (e.g., <10 Hz) they are considered to be relatively insignificant. Thus the error in the model, E, is a good approximation for most of the system noise.

Patient muscle effort, however, is an example of a non-random noise source that may have significant implications for the accuracy of the model. In a spontaneously breathing patient using a ventilator, the driving pressure at any time is generated by both the ventilator ($P_v$) and the patient's respiratory muscles ($P_{mus}$):

$$P_{tot} = P_v + P_{mus}$$

Because $P_{mus}$ may not be measured directly without using an esophageal balloon catheter, it is difficult to accurately determine the mechanical parameters non-invasively while the patient's muscles are activated. Predominantly this is a concern during inspiration when the diaphragm and accessory muscles contract. Fitting flow and volume data to ventilator pressure data during inspiration without consideration of muscle activity would underestimate resistance and overestimate compliance:

$$P_v = R\dot{V}(t) + \frac{V(t)}{C} + P_0$$

This approach, which may be implemented by a processor in an MLR process, may allow the exclusion of influences from patient effort that would otherwise impede the accuracy of R and C.

Optionally, data used for the regression in each breath may include the beginning of expiration up to the point when approximately 85-95% (or more preferably 90%) of the tidal volume had been expired. Thus, in some embodiments only a portion (e.g., an expiratory portion) of a breathing cycle (e.g., the pressure, flow and volume measures attributable or corresponding with the expiratory portion), may be evaluated from an initial time of expiration up to a time when a desired limit (e.g., a range of 85-90 percent) of expired tidal volume is reached. A reason for this may be to optimally capture the dynamic behavior in the data. The intention of fitting the data to this model is to describe the dynamics of the passive system subjected to the pressure source. Thus, the calculations may exclude data that could be associated with patient respiratory muscle activity. Where slow flow occurs at end-expiration accompanying minimal change in pressure, the increased signal to noise ratio has the potential to introduce inaccuracy in the parameter estimation, and so this portion of the data may be omitted from the computation.

The desire for a good fit is to achieve an expiratory breath without expiratory effort or other spurious artifacts, such that the flow waveform follows an exponential decay. Thus, it may be desirable to preclude artifactual breaths from involvement with the fitting algorithm. Thus, in some embodiments, an accuracy assessment of the determination of resistance and compliance may be implemented. One way to accomplish this may be to implement a median filter, such as one with a width of about 15, such that the median values of the fitted mechanics parameters from the last number breaths (e.g., about 15) can be taken to represent the expiratory breaths with more regular exponential decay. Also a coefficient of determination $R^2$ value from the statistical fit may be used as a criterion to eliminate poorly fitted breaths. For example, a threshold of about 0.8 may be used. Thus, in such an example, a processor of an apparatus may determine accuracy, such as by determining the coefficient of determination $R^2$ value for each MLR determination of compliance and resistance values and comparing the value against with an accuracy threshold, so that certain determinations of resistance and compliance may be disregarded (e.g., determinations where the coefficient does not equal or exceed the threshold).

Patient-Effort Model

In some embodiments, rather than or in addition to implementing the flow subtraction model previously discussed, synchronization or cycling criteria may also be based on a patient-effort model as herein discussed. In this regard, both the flow-subtraction and patient-effort models for cycling may adopt a similar overall approach to achieve a common outcome. Each can mathematically model the patient-ventilator system in order to isolate the activity of the patient's inspiratory activity, and thereby glean knowledge of when to terminate the mechanical breath or inspiratory positive airway pressure level. Both methodologies can be based on the linear single compartment model of the patient respiratory system with a given or determined Resistance (R) and Compliance (C). In such cases, the total instantaneous pressure at the system inlet at a given time point (t) i.e. airway pressure, can be expressed by the equation of motion of the respiratory system, such as equation 1A above or as follows:

$$P(t) = \frac{V(t)}{C} + R \cdot \dot{V}(t) + PEEP_{TOT}$$

where V(t) is the insufflated tidal volume at time point (t) and $\dot{V}(t)$ is the inspiratory flow rate, and $PEEP_{TOT}$ is the total end-expiratory pressure including both applied PEEP from the ventilator and intrinsic PEEP, PEEPi. Inertance can be neglected in this model, due to its extremely low value at respiratory rates less than 2 Hz. During PSV, P(t) is the sum of the driving pressure support applied by the ventilator ($P_{PS}$) and the patient's respiratory muscles ($P_{mus}$), $$P_{PS}(t) + P_{mus}(t) = \frac{V(t)}{C} + R \cdot \dot{V}(t) + PEEP_{TOT} \quad \text{equation (J1)}$$

where the pressure support $P_{PS}$ is effectively the total measured airway pressure, Paw, minus the applied ventilator PEEP. In applying this theory to inverse modeling the patient's effort, factors related to its timing can be measured. This information is useful in manipulating the ventilator's switching algorithms. Because the concern here it primarily with the time-course of patient activity, an accurate estimate of intrinsic PEEP is not needed as it is effective only in offsetting the magnitude and any time-dependent fluctuations are considered as being of very low frequency. Therefore for simplicity in the model, the effects of PEEPi may optionally be ignored. A significant aspect of applying this inverse-model approach to cycling the ventilator is that some knowledge of the patient's lung mechanics, R and C, may be required. Information regarding either R, C or patient time constant τp (=R×C) when implemented in some of the cycling algorithms described here, can be provided by automated algorithms for estimating respiratory mechanics such as those as previously described.

An automated cycling algorithm based on the patient-effort model (PEM) can take advantage of equation J2 in finding a numerical solution to estimating patient muscle effort. For example, by rearranging the equation in terms of patient effort and ignoring the effects of PEEPtot as follows:

$$P_{mus}(t) = \frac{V(t)}{C} + R \cdot \dot{V}(t) + PEEP_{TOT} - P_{aw}(t) \quad \text{equation (J2)}$$

Values may be substituted to solve the equation, including applied ventilator PEEP, instantaneous measurement of the airway pressure, Paw, as well as measured inspiratory flow, $\dot{V}(t)$, its integral, tidal volume, V(t), and estimated values of R and C such as those determined by the methods previously discussed. This results in an estimate of the time-varying course of patient muscle effort, $Pmus_{est}$, which may be calculated in real time and may be based on a system having: a) reasonable measures of the patient's resistance and compliance used as input; b) a reliable estimate of total flow that is compensated for unintentional leak; and, c) pressure at the airway opening can be measured or estimated accurately taking into account impedance losses of the ventilator circuit. With such a system, the method may be applied in any ventilator or respiratory treatment apparatus without requiring a pre-existing model of its behavior.

Figure 9A:
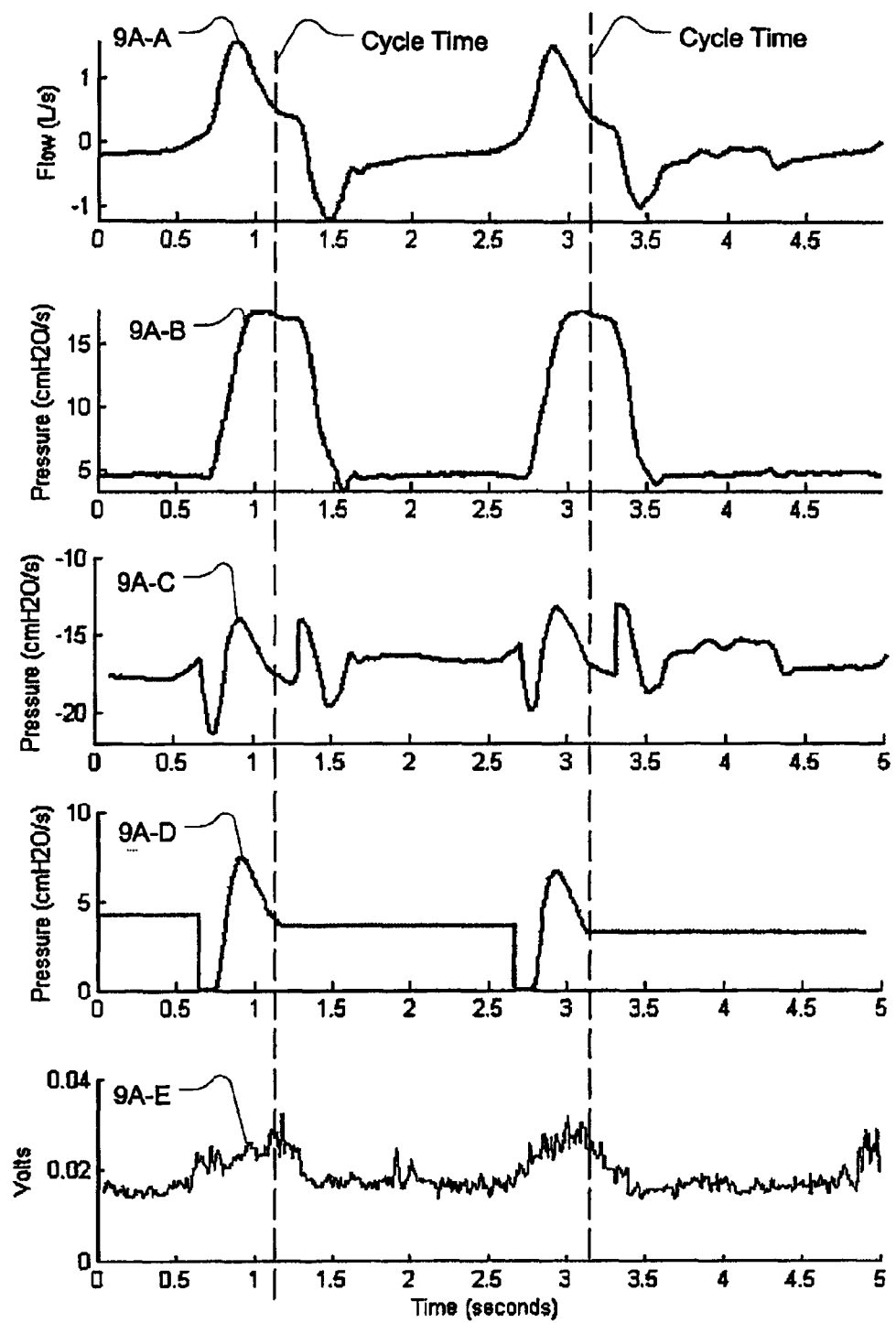
FIG. 9A is a graph of several signals relating to patient-effort model cycling in some embodiments of the current technology.

FIG. 9A illustrates implementation of a cycling algorithm based on the principle of the patient-effort model cycling. The signals of the five graphs are shown on a common time scale. The data was taken from an obstructive patient on PSV with traditional cycling set at 25% of the peak flow. Patient flow, pressure at the airway, and diaphragmatic EMG are the measured physiological signals and are shown in traces 9A-A, 9A-B and 9A-E respectively. The above model is used to derive estimated patient effort $Pmus_{est}$ shown in trace 9A-C (e.g., equation J2). Due to the inertial effects of the ventilator pressure transitions which are not accounted for in this example model, artifacts are commonly observed on this signal. An effort related synchronization control signal may be derived from $Pmus_{est}$ such as signal $P_{control}$ (shown as trace 9A-D in FIG. 9A), which may be used for determining a ventilator cycle point. The control signal can be derived to include rescaled positive values of $Pmus_{est}$ after the ventilator triggers into inspiration. As illustrated in FIG. 9A, the vertical dashed lines labeled "cycle time" show the cycle point that can be detected from the below methodology with the control signal. As illustrated, this detection correlates well with the end of true patient inspiratory activity indicated by in the signal of EMGdi at 9A-E.

An example process for the control signal is as follows:

1. As soon as the ventilator triggers, such as upon detection of the beginning of patient inspiration, $P_{control}$ can be set to 0 in the case of a first cycle, or reset to zero in the case of subsequent cycles (e.g., $P_{control}=0$)

2. If Pmus is not increasing, such that if $Pmus_{est}$ (n+1) <$Pmus_{est}$ (n), then $P_{control}$ is set to 0 (e.g. $P_{control}=0$).

3. As soon as a local minimum is found and $Pmus_{est}$ starts to increase, $P_{control}$ is set to the $Pmus_{est}$ (e.g., $P_{control}=Pmus_{est}$).

4. The peak value of $P_{control}$, (i.e., $P_{conMAX}$), is located by running a peak detection algorithm on the signal during inspiration. For example, for each timed sample n, if $P_{control}$ (n)>$P_{conMAX}$, then $P_{conMAX}=P_{control}$(n).

5. The end of neural inspiration may optionally be defined by some threshold such as the point 50% below the apogee or peak effort within a breath. The cycling criterion may therefore be set at a percentage (e.g., 50%) of the $P_{conMAX}$, within the breath such that the ventilator transitions to expiration when $P_{control}$ is equal to or less than this value. Thus, the peak value may be calculated each time within each breath and then used as a part of a cycling decision in that breath.

The vertical dashed lines for the two breaths in FIG. 9A show the predicted 50% cycle point of $P_{conMAX}$. This corresponds to the peak level of $EMG_{di}$ which is the standard indication of the neural termination of inspiration. During expiration, $P_{control}$ is inactive and assumes an arbitrary and constant value.

With such a methodology, a respiratory treatment apparatus may simply and non-invasively utilize a pressure sensor and flow sensor in the patient interface (or other locations such as in the flow generator and include compensation calculations to determine the flow and pressure within the patient interface) to determine the estimated effort with equation J2 and based thereon synchronize the cycling of the apparatus using the related control signal derived from the estimated effort $Pmus_{est}$. As such, it can be implemented without EMG sensors.

However, in other embodiments a directly measured Pmus may be utilized and the $P_{control}$ signal according to the methodology described above may be derived from the measured Pmus. For example, a sensor, such as an electro-optical sensor for non-invasively measuring diaphragmatic muscle activity, may be implemented to determine a signal indicative of Pmus. Such a transducer may pave the way for better non-invasive detection of patient effort. One such device may be that of Chianura and Giardini (2010) (Chianura, A. & Giardini, M. E. (2010), 'An electrooptical muscle contraction sensor.', Med Biol Eng Comput 48(7), 731-734. The electro-optical sensor may be implemented to detect muscle contraction. This is based on the principle that the muscle undergoes blood-depletion during contraction, and this correlates with its infra-red optical absorption. Its advantages over surface diaphragmatic EMG include the reduction of noise and other artifacts. Such a device may be integrated with a ventilator or respiratory treatment apparatus, and used as a measure of diaphragm and accessory muscle contraction during inspiration. Thus, the sensor may be implemented to improve control of triggering and cycling. In particular, it may offer an advantage as a non-invasive alternative to neural adjust ventilatory assistance (NAVA), which is a mode favored for its ability to synchronize, but which requires invasive use of electrodes.

Example Controller/Processing Apparatus Architecture

Figure 10:
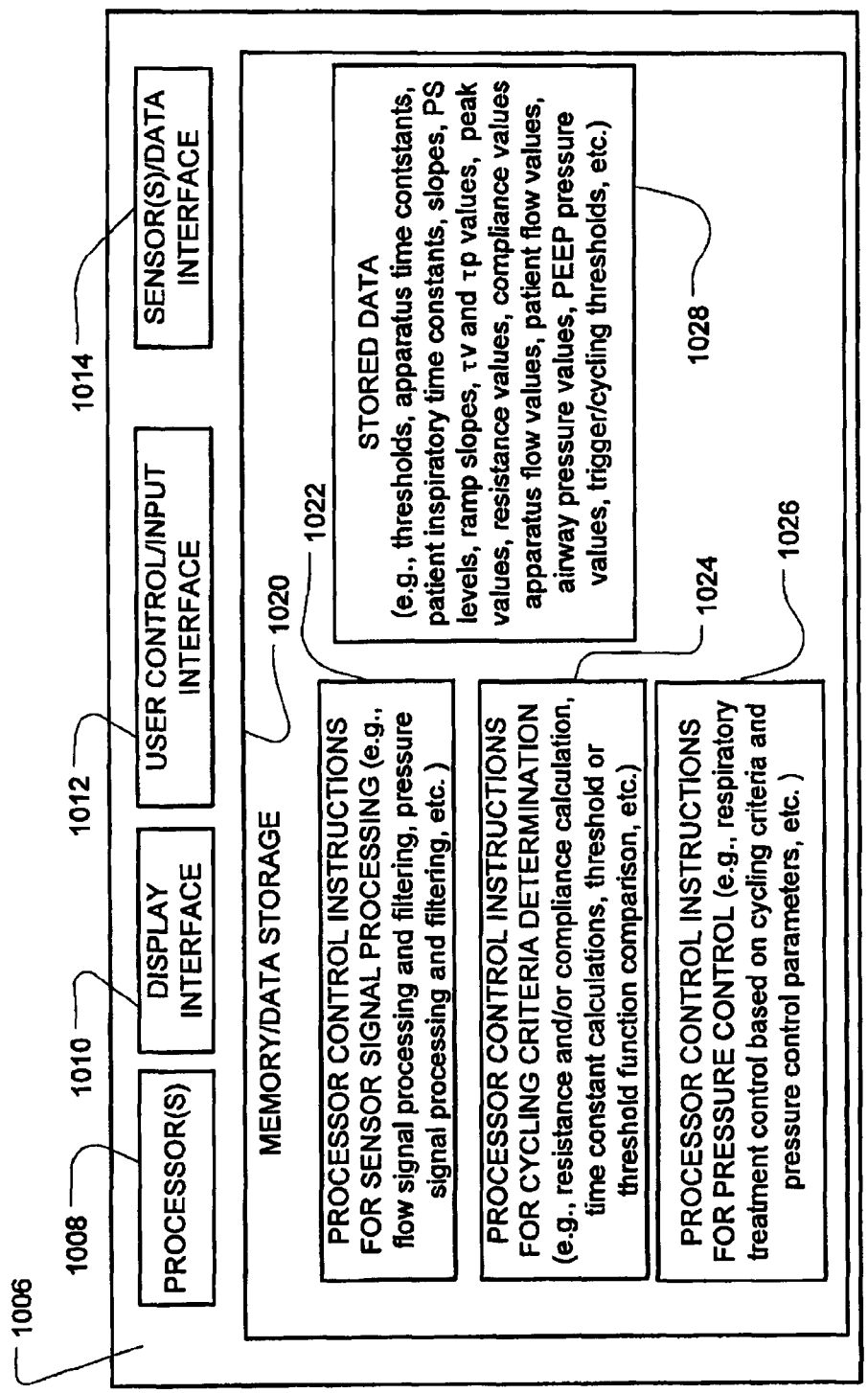
FIG. 10 is a block diagram illustrating suitable components that may be implemented as a processing apparatus or controller for embodiments of the present technology.

An example system architecture of a processing apparatus (e.g., computer or controller 1006) is illustrated in the block diagram of FIG. 10. The system architecture may serve as a respiratory treatment apparatus controller with the cycle detection technology as discussed herein or more simply as a controller for a stand alone cycle detector, patient muscle generated flow detector or cycle criteria detector such as a monitoring device. Thus, the controller 1006 may include one or more processors programmed to implement particular methodologies or algorithms described in more detail herein. To this end, the controller may include integrated chips, a memory and/or other control instruction, data or information storage medium. For example, programmed instructions encompassing such a control methodology may be coded on integrated chips in the memory of the device. Such instructions may also or alternatively be loaded as software or firmware using an appropriate data storage medium.

The controller 1006, which may also optionally be implemented by a general purpose computer, may include one or more programmable processors 1008. The device may also include a display interface 1010 to output data from the detection methodologies as previously discussed (e.g., patient attributable flow data, apparatus attributable flow data, cycle criteria, estimated muscle effort and related information, etc.), results, traces, signals or graphs as described or illustrated herein to a display such as on a monitor or LCD panel. A user control/input interface 1012, for example, for a keyboard, touch panel, control buttons, mouse etc. may also be included for inputting data, or otherwise activating, setting or operating the methodologies described herein. The device may also include a sensor or data interface 1014, such as a bus, for receiving/transmitting data such as programming instructions, flow data, pressure data, apparatus and patient time constants, settings data, calculation algorithms, and other output or input of the previously described methodologies.

The device also typically includes memory/data storage components 1020 containing control instructions and data of the aforementioned methodologies and algorithms. Thus, at 1022, these may include stored processor control instructions for sensor signal processing. For example, these may include instructions for flow signal processing and filtering, pressure signal processing and filtering, etc. At 1024, they may also include stored processor control instructions for cycling criteria determination such as the determinations and calculations previously described with regard to patient cycle detection and/or the conditions associated with the described expiratory pressure triggering and/or the detection of patient generated flow and apparatus generated flow. At 1026, they may also include processor control instructions for pressure treatment control based on the cycling criteria discussed herein, such as respiratory treatment control parameters, pressure support control parameters or pressure treatment adjustment methodologies. Finally, they may also include stored data at 1028, which may include input and output of the processing algorithms or methodologies previously described. For example, this may include cycling or other thresholds, apparatus time constants, patient inspiratory time constants, slopes, PS levels, ramp slopes, $\tau V$ and $\tau p$ values, peak values, resistance values, compliance values, apparatus flow values, patient flow values, airway pressure values, PEEP pressure values, trigger/cycling thresholds, total flow-volume curves, apparatus attributable flow-volume curves, patient respiratory muscle attributable flow-volume curves, estimated patient effort ($Pmus_{est}$), $P_{control}$, etc.

In some embodiments, some or all of the processor control instructions and data for controlling the above described methodologies may be contained in a computer readable recording medium as software for use by a general purpose computer so that the general purpose computer may serve as a specific purpose computer according to any of the methodologies discussed herein upon loading the software into the general purpose computer.

In the foregoing description and in the accompanying drawings, specific terminology, equations and drawing symbols are set forth to provide a thorough understanding of the present technology. In some instances, the terminology and symbols may imply specific details that are not required to practice the technology. For example, although the terms "first" and "second" have been used herein, unless otherwise specified, the language is not intended to provide any specified order but merely to assist in explaining distinct elements of the technology. Furthermore, although process steps in the methodologies have been illustrated in the figures and description in an order, such an ordering is not necessarily required. Those skilled in the art will recognize that such ordering may be modified and/or aspects thereof may be conducted in parallel.

Moreover, although the technology herein has been described with reference to particular embodiments, it is to be understood that these embodiments are merely illustrative of the principles and applications of the technology. It is therefore to be understood that numerous modifications may be made to the illustrative embodiments and that other arrangements may be devised without departing from the spirit and scope of the technology. For example, some of the embodiments herein have been described for purposes of implementation in a ventilator such as a Pressure Support Ventilator, or other type of ventilator for treatment of lower airway obstruction or other respiratory insufficiency disease (e.g., COPD). However, it may also be implemented for making changes to pressure in other pressure treatment apparatus such as bi-level PAP, PAP with expiratory pressure relief, or other flow or pressure treatment device, such as for the treatment of sleep disordered breathing, where pressure or flow changes of a flow generator are intended to be synchronized with patient respiration.

The invention claimed is:

1. An automated processing method for adapting cycling of a respiratory treatment apparatus that controls a delivery of a synchronized respiratory treatment to a patient, the method comprising:
    controlling generation of inspiratory pressure and expiratory pressure over a first plurality of cycles with a processor, wherein timing of delivery of the expiratory pressure for the first plurality of cycles is based on first cycling criteria; and
    controlling generation of inspiratory pressure and expiratory pressure over a second plurality of cycles subsequent to the first plurality of cycles with the processor, wherein timing of delivery of the expiratory pressure for the second plurality of cycles is based on second cycling criteria, the second cycling criteria being different from the first cycling criteria and initiated for operation subsequent to the first plurality of cycles,
    wherein the second cycling criteria are determined during the first plurality of cycles, and
    wherein each of the first and second cycling criteria controls synchronization of the respiratory treatment with the patient's breathing cycle.

2. The method of claim 1 wherein the second cycling criteria comprise a function of a first inspiratory flow measure and a second inspiratory flow measure, the second inspiratory flow measure attributable to the respiratory treatment apparatus,
    in which each of the first inspiratory flow measure and the second inspiratory flow measure is from a sensor.

3. The method of claim 2 wherein the first cycling criteria comprise comparing an instantaneous flow measure to a threshold proportion of a peak flow.

4. The method of claim 1 wherein the first plurality of cycles comprises a learning period that is configured for determining and storing values for control of treatment in a plurality of subsequent treatment sessions.

5. The method of claim 1 wherein the first plurality of cycles comprises a learning period that is initiated in a current treatment session.

6. The method of claim 1 wherein the second cycling criteria comprise an inspiratory time constant.

7. The method of claim 6 wherein the inspiratory time constant is a function of a determined slope of an expiratory portion of a measured flow from the first plurality of cycles.

8. The method of claim 7 wherein the inspiratory time constant is a mean of a plurality of determined slopes of expiratory portions of the measured flow from the first plurality of cycles.

9. The method of claim 6 wherein the inspiratory time constant is from a measured flow from the first plurality of cycles and is a measured time for a proportion of a tidal volume to be delivered to the patient in a cycle of the first plurality of cycles.

10. The method of claim 9 wherein the inspiratory time constant is a mean of measured times for a proportion of a tidal volume to be delivered to the patient in the first plurality of cycles.

11. The method of claim 6 wherein a determination of the inspiratory time constant comprises a multiple linear regression process to fit pressure, flow and volume data for determining a measure of resistance and compliance.

12. The method of claim 2 wherein the function of the first inspiratory flow measure and the second inspiratory flow measure comprises an equality of the first inspiratory flow measure and the second inspiratory flow measure.

13. The method of claim 2 wherein the function of the first inspiratory flow measure and the second inspiratory flow measure comprises a calculated difference of the first inspiratory flow measure and the second inspiratory flow measure.

14. The method of claim 2 wherein the second inspiratory flow measure is a function of a determined flow peak, a calculated respiratory resistance and a pressure treatment setting.

15. A respiratory treatment apparatus for cycling synchronized respiratory pressure treatment to a patient, the apparatus comprising:
a patient interface to direct a breathable gas;
a flow generator coupled with the patient interface to generate the breathable gas in inspiratory and expiratory pressure cycles through the patient interface;
a flow sensor to provide a signal indicative of flow through the patient interface;
a processor, coupled with the flow generator and the flow sensor, the processor configured to control:
generation of inspiratory pressure and expiratory pressure over a first plurality of cycles, wherein timing of delivery of the expiratory pressure for the first plurality of cycles is based on first cycling criteria; and
generation of inspiratory pressure and expiratory pressure over a second plurality of cycles subsequent to the first plurality of cycles, wherein timing of delivery of the expiratory pressure for the second plurality of cycles is based on second cycling criteria, the second cycling criteria being different from the first cycling criteria and initiated for operation subsequent to the first plurality of cycles,
wherein the second cycling criteria are determined during the first plurality of cycles, and
wherein each of the first and second cycling criteria controls synchronization of the respiratory treatment with the patient's breathing cycle.

16. The apparatus of claim 15 wherein the second cycling criteria comprise a function of a first inspiratory flow measure from the flow sensor and a second inspiratory flow measure from a second sensor attributable to the respiratory treatment apparatus.

17. The apparatus of claim 16 wherein the first cycling criteria comprise comparing an instantaneous flow measure to a threshold proportion of a peak flow.

18. The apparatus of claim 15 wherein the first plurality of cycles comprises a learning period that is configured for determining and storing values for control of treatment in a plurality of subsequent treatment sessions.

19. The apparatus of claim 15 wherein the first plurality of cycles comprises a learning period that is initiated in each treatment session.

20. The apparatus of claim 15 wherein the second cycling criteria comprise an inspiratory time constant.

21. The apparatus of claim 20 wherein the inspiratory time constant is a function of a determined slope of an expiratory portion of a measured flow from the first plurality of cycles.

22. The apparatus of claim 21 wherein the inspiratory time constant is a mean of a plurality of determined slopes of expiratory portions of the measured flow from the first plurality of cycles.

23. The apparatus of claim 20 wherein the inspiratory time constant is from a measured flow from the first plurality of cycles and is a measured time for a proportion of a tidal volume to be delivered to the patient in a cycle of the first plurality of cycles.

24. The apparatus of claim 23 wherein the inspiratory time constant is a mean of measured times for a proportion of a tidal volume to be delivered to the patient in the first plurality of cycles.

25. The apparatus of claim 20 wherein the inspiratory time constant is calculated as a function of resistance and compliance values determined by a multiple linear regression process with pressure, flow and volume data.

26. The apparatus of claim 16 wherein the function of the first inspiratory flow measure and the second inspiratory flow measure comprises an equality of the first inspiratory flow measure and the second inspiratory flow measure.

27. The apparatus of claim 16 wherein the function of the first inspiratory flow measure and the second inspiratory flow measure comprises a calculated difference of the first inspiratory flow measure and the second inspiratory flow measure.

28. The apparatus of claim 16 wherein the second inspiratory flow measure is a function of a determined flow peak, a calculated respiratory resistance and a pressure treatment setting.

* * * * *